US009982020B2

(12) United States Patent
Bashkin et al.

(10) Patent No.: US 9,982,020 B2
(45) Date of Patent: May 29, 2018

(54) ANTIVIRAL COMPOUNDS AND METHODS FOR TREATING INFECTIONS CAUSED BY DOUBLE-STRANDED DNA VIRUSES

(71) Applicants: NanoVir LLC, Kalamazoo, MI (US); THE CURATORS OF THE UNIVERSITY OF MISSOURI, Columbia, MO (US)

(72) Inventors: James K. Bashkin, St. Louis, MO (US); Terri Grace Edwards, Kalamazoo, MI (US); Christopher Fisher, Kalamazoo, MI (US); George D. Harris, Jr., Chesterfield, MO (US); Kevin J. Koeller, Richmond Heights, MO (US)

( * ) Notice: Subject to any disclaimer, the term of this patent is extended or adjusted under 35 U.S.C. 154(b) by 0 days. days.

(21) Appl. No.: 14/818,881

(22) Filed: Aug. 5, 2015

(65) Prior Publication Data

US 2015/0329596 A1    Nov. 19, 2015

Related U.S. Application Data

(63) Continuation-in-part of application No. 13/649,000, filed on Oct. 10, 2012, now Pat. No. 9,133,228.

(60) Provisional application No. 62/033,315, filed on Aug. 5, 2014, provisional application No. 61/545,311, filed on Oct. 10, 2011.

(51) Int. Cl.
| | |
|---|---|
| *A61K 31/415* | (2006.01) |
| *C07K 14/00* | (2006.01) |
| *C07K 7/02* | (2006.01) |
| *A61K 38/00* | (2006.01) |

(52) U.S. Cl.
CPC ............ *C07K 14/00* (2013.01); *C07K 7/02* (2013.01); *C07K 14/001* (2013.01); *C07K 14/003* (2013.01); *A61K 38/00* (2013.01)

(58) Field of Classification Search
USPC .......................................... 514/397; 530/323
See application file for complete search history.

(56) References Cited

U.S. PATENT DOCUMENTS

| | | | |
|---|---|---|---|
| 5,616,606 A | 4/1997 | Lown et al. | |
| 6,673,940 B1 | 1/2004 | Dervan et al. | |
| 6,958,240 B1 | 10/2005 | Baird et al. | |
| 7,589,171 B2 * | 9/2009 | Bashkin ................ | A61K 38/02 435/6.1 |
| 8,119,677 B2 * | 2/2012 | Bashkin ................ | A61K 38/02 514/397 |
| 8,524,899 B2 | 9/2013 | Dervan et al. | |
| 8,993,609 B2 * | 3/2015 | Bashkin ................ | A61K 38/16 514/397 |
| 9,133,228 B2 * | 9/2015 | Bashkin ................ | C07K 14/003 |
| 9,290,551 B2 * | 3/2016 | Bashkin ................ | A61K 38/16 |
| 2003/0109448 A1 | 6/2003 | Crowley et al. | |
| 2003/0119891 A1 | 6/2003 | Phillion et al. | |
| 2004/0171799 A1 | 9/2004 | Sugiyama et al. | |
| 2005/0009054 A1 | 1/2005 | Phillion et al. | |
| 2012/0225809 A1 | 9/2012 | Bashkin et al. | |

FOREIGN PATENT DOCUMENTS

| | | |
|---|---|---|
| WO | WO9835702 | 8/1998 |
| WO | WO9837066 | 8/1998 |
| WO | WO9837067 | 8/1998 |
| WO | WO9850058 | 11/1998 |
| WO | WO0015773 | 3/2000 |
| WO | WO2004099131 | 11/2004 |
| WO | WO2005033282 | 4/2005 |
| WO | WO2007045096 | 4/2007 |
| WO | WO2007103584 | 9/2007 |
| WO | WO2007130616 | 11/2007 |

OTHER PUBLICATIONS

Wetzler, Diana, E., et al., "New human papilloma virus E2 transcription factor mimics: A tripyrrole-peptide conjugate with tight and specific DNA-recognition", PLOS ONE, vol. 6, No. 7, Jul. 2011, pp. 2-9/E.
Buchmueller, et al., "Molecular recognition of DNA base pairs by the formamido pyrrole and formamido imidazole pairings in stacked polyamides", Nucleic Acids Research, 912-921, 2005, vol. 33, No. 3.
Coull, et al., "Targeted Derepression of the Human Immunodeficiency Virus Type 1 Long Terminal Repeat by Pyrrole-Imidazole Polyamides", Journal of Virology, Dec. 2002, pp. 12349-12354.
Crowley, et al., "Controlling the Intracellular Localization of Fluorescent Polyamide Analogues in Cultured Cells", Bioorganic & Medicinal Chemistry Letters, 13, 2003, pp. 1565-1570.
Dervan, et al., "Recognition of the DNA minor groove by pyrroleimidazole polyamides" Current Opinion in Structural Biology, 2003, 13, pp. 284-299.
Edelson, et al., "Influence of structural variation on nuclear localization of DNA-binding polyamide-fluorophore conjugates", Nucleic Acids Research, 2004, vol. 32, No. 9, pp. 2802-2818.
Edwards, Terri, G., et al., HPV episome levels are potently decreased by pyrrole-imidazole polyamides, Antiviral Research, 91, 2011, pp. 177-186.
Extended European Search Report for EP12840685.7 dated Mar. 10, 2015.
Groeger, K et al., Guanidiniocarbonyl-pyrrole-aryl conjugates as nucleic acid sensors: switch of binding mode and spectroscopic responses by introducing additional binding sites into the linker. Org. Biomol. Chem., vol. 9, pp. 198-209, 2011.
Groger, Kathrin, et al., Guanidiniocarbonyl-pyrrole-aryl conjugates as nucleic acid sensors: switch of binding mode and spectroscopic responses by introducing additional binding sites into the linker, Org. Biomol. Chem., 2011, vol. 9, pp. 198-209.
Jacobs, Claire, S., et al., Modifications at the C-Terminus to improve pyrrole-imidazole polyamide activity in cell culture, J. Med. Chem., vol. XXX, pp. A-I, publilshed on Jul. 2, 2009 on http://pubs.acs.org.

(Continued)

*Primary Examiner* — Rei Tsang Shiao
(74) *Attorney, Agent, or Firm* — Hueschen and Sage

(57) ABSTRACT

The present invention relates to polyamide compounds and their use in pharmaceutical compositions and in medical applications for the treatment of human papillomavirus infections and/or polyomavirus infections.

4 Claims, 10 Drawing Sheets

(56) References Cited

OTHER PUBLICATIONS

Khalal, Abedawn, I., et al., Amide isosteres in structure-activity studies of antibacterial minor groove binders, European Journal of Medicinal Chemistry, 46, 2011, pp. 5343-5355.
Livengood, et al., Paradoxical effects of DNS binding polyamides on HTLV-1 transcription, Frontiers in Bioscience, 9, Sep. 1, 2004, pp. 3058-3067.
Lown, et al., "Novel linked antiviral and antitumor agents related to netropsin and distamycin. Synthesis and biological evaluation", J. Med. Chem., 1989, 32, pp. 2368-2375.
Marques, et al., "Expanding the Repertoier of Heterocycle Ring Pairs for Programmable for Minor Groove DNA Recognition", J. Am. Chem. Soc., 2004, 126, pp. 10339-10349.
Martinez, Thomas, F., et al., Replication stress by Py-Im polyamides induces a non-canonical ATR-dependent checkpoint response, Nucleic Acids Research, Sep. 23, 2014, pp. 1-14.
Muzikar, Katy, A., et al., Expanding the repertoire of natural product-inspired ring pairs for molecular recognition of DNA, Organic Letters, 2011, vol. 13, No. 20, pp. 5612-5615.
Nickols, et al., "Improved nuclear localization of DNA-binding polyamides", Nucleic Acids Research, 2007, vol. 35, No. 2, pp. 363-370.
Nishijima, S., et al., "Cell permeability of Py-Im-polyamide-fluorescein conjugates: Influence of molecular size and Py/Im content", Bioorganic & Medicinal Chemistry, 2010, 18, pp. 978-983.
O'Hare, et al., "DNA sequence recognition in the minor groove by crosslinked polyamides the effect of N-terminal head group and linker length on binding affinity and specificity", Proc. Natl. Acad. Sci. USA, 2002, vol. 99, No. 1, pp. 72-77.
Philips, Brian, J., et al., DNA Damage effects of a polyamide-CBI conjugate in SV40 virions, Molecular Pharmacology, 67, 2005, pp. 877-882.

Renneberg, et al., "Imidazopyridine Pyrrole and Hydroxybenzimidazole Pyrrole Pairs for DNA Minor Groove Recognition", J. Am. Chem. Soc., 2003, 125, pp. 5707-5716.
Schaal, et al., "Inhibition of human papilloma virus E2 DNA binding protein by covalently linked polyamides", Nucleic Acids Research, vol. 31, No. 4, 2003, pp. 1282-1291.
Tsai, et al., "Unanticipated differences between {alpha}- and {gamma}-diaminobutyric acid-linked hairpin polyamide-alkylator conjugates", Nucleic Acids Research, 2007, vol. 35, No. 1, pp. 307-316.
Turner, et al., "Aliphatic Aromatic Amino Acid Pairings for Polyamide Recognition in the Minor Groove of DNA", J. Am. Chem. Soc., 1998, 120, pp. 6219-6226.
Turner, et al., "Recognition of Seven Base Pair Sequences in the Minor Groove of DNA by Ten-Ring Pyrrole-Imidazole Polyamide Hairpins", J. Am. Chem. Soc., 1997, 119, pp. 7636-7644.
Wang, Tong-Dong, et al., DNA crosslinking and biological activity of a hairpin polyamide-chlorambucil conjugate, Nucleic Acids Research, vol. 31, No. 4, 2003, pp. 1208-1215.
White, Peter, et al., "Inhibition of Human Papillomavirus DNA Replication by Small Molecule Antagonists of the E1 E2 Protein Interaction", The Journal of Biological Chemistry, vol. 278, No. 29, Jul. 18, 2003, pp. 26765-26772.
Yasuda, Ai, et al., CNA ligand designed to antagonize EBNA1 represses Epstein-Barr virus-induced immortalization, Cancer Science, Dec. 2011, vol. 102, No. 12, pp. 2221-2230.
Zhan, et al., "Alternative heterocycles for dna recognition. a 3-pyrazole pyrrole pair specifies for g•c base pairs", Bioorganic & Medicinal Chemistry, 2000, 8, pp. 2467-2474.
Zhang, et al., "Discrimination of Hairpin Polyamides with an a-Substituted-?-aminobutyric Acid as a 5'-TG-3' Reader in DNA Minor Groove", J. Am. Chem. Soc., 2006, 128, pp. 8766-8776.

* cited by examiner

Guanidinyl Radical $R^{1-4} = H$

Tautomer $R^1$ = alkyl, aryl, aralkyl
$R^{2-4} = H$

Tautomers $R^{1,2}$ = alkyl, aryl, aralkyl
$R^{3,4} = H$

Tautomer

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: PRIMER

<400> SEQUENCE: 1
```

```
cctccgttaa ggttcgtagg tca                                          23

<210> SEQ ID NO 2
<211> LENGTH: 17
<212> TYPE: DNA
<213> ORGANISM: Artificial Sequence
<220> FEATURE:
<223> OTHER INFORMATION: PRIMER

<400> SEQUENCE: 2
cagcgctcac accagtc                                                 17

<210> SEQ ID NO 3
<211> LENGTH: 35
<212> TYPE: DNA
<213> ORGANISM: Artificial Sequence
<220> FEATURE:
<223> OTHER INFORMATION: PROBE

<400> SEQUENCE: 3
attgaagtgc aacttgcatc tgttgctact gttga                             35
```

US 9,982,020 B2

ANTIVIRAL COMPOUNDS AND METHODS FOR TREATING INFECTIONS CAUSED BY DOUBLE-STRANDED DNA VIRUSES

FEDERALLY SPONSORED RESEARCH OR DEVELOPMENT

This invention was developed, in part, with government funding under Grant Numbers R41 AI068159, R01 AI083803 and 2R42AI068159 awarded by the National Institutes of Health. The United States Government may have certain rights in this invention.

BACKGROUND OF THE INVENTION

The present invention relates to polyamide compositions and therapies for treatment of cells and tissues infected with double stranded DNA viruses, for example, human papillomaviruses (HPV) and/or polyomaviruses (PyV).

A significant part of the viral life cycle of many DNA viruses has them maintained as double-stranded, closed circular, supercoiled, chromatinized DNAs within the nucleus. Among these viruses are a number of types that cause a significant disease burden including papillomaviruses, polyomaviruses, Epstein Barr virus (EBV), and hepatitis B virus (HBV), a member of the genus *Orthohepadnavirus*.

Polyomaviruses (PyV) are a family of small (~5 KB), non-enveloped DNA viruses that occupy a broad replicative niche in vertebrates from birds to humans, but individually have a narrow species tropism. Simian virus 40 (SV40), an archetypal PyV was first discovered as a tumor-inducing virus in rhesus monkey kidney cells cultures (1) and subsequently became an important tool for studying DNA replication, repair, and oncogenesis. Recent years have seen considerable growth of the number of known polyomaviruses, with human polyomaviruses (HPyV) now numbering over ten (2). HPyV are suspected etiological agents in a number of cancers, but only MCPyV has been definitively associated with the rare and aggressive Merkel Cell carcinoma (3).

PyV often persist as latent infections without causing disease, but reactivation of the infection may lead to disease in a variety of tissues. For example, reactivation of PyV in immunocompromised patients is a growing area of concern. BK polyomavirus (BKV) is the major cause of polyomavirus-associated nephropathy (PyVAN) causing 1-15% of kidney transplant patients to be at risk of premature allograft failure (4). There are a growing number of PyVAN patients due to increases in the numbers of renal transplants and the development of more effective immunosuppressive drugs (5). Likewise, 10-25% of bone marrow transplant (BMT) patients are susceptible to hemorrhagic cystitis of the bladder and lower urinary tract that is largely attributable to BKV reactivation due to immunosuppression (6).

Progressive multifocal leukoencephalopathy (PML) is a rare, but typically fatal, inflammation of the white matter of the brain in multiple locations that is attributable to JC polyomavirus (JCV) (7). PML is typically associated with JCV reactivation in severely immunocompromised patients such as those receiving immunosuppressive therapy following transplant, following chemotherapy, or in those with AIDS. Other HPyV are also associated with morbidity following reactivated in immunocompromised patients. Merkel cell polyomavirus (MCPyV), for example, has been implicated as the etiological agent in Merkel cell carcinoma, a cancer with a strikingly high incidence in AIDS; chronic lymphocytic leukemia (CLL) patients; and in immunosuppressed organ transplant patients, including but not limited to bone marrow transplant recipients (7). There are currently few antiviral treatment options for polyomaviruses and so antiviral therapies would be an important advancement for diseases associated with these viruses (7).

HBV is a small (~3.2 KB), enveloped DNA virus that infects hepatocytes and replicates by way of an RNA intermediate (8). The encapsidated viral genome consists of 3.2 kB of relaxed, circular DNA which is converted to covalently, closed, circular DNA (cccDNA) upon its translocation to the nucleus. Chronic infection by HBV contributes to a number of diseases of the liver including hepatitis with progression to cirrhosis and hepatocellular carcinoma (9). More than 240 million people are infected with HBV, and 780,000 people die annually due to the consequences of HBV infection (10). There is no specific treatment for HBV although some patients can be treated with Interferon or antiviral agents to slow the progression of the disease. Seven drugs have been licensed by the FDA, to date, for the treatment of chronic hepatitis B infection: interferon-alpha and pegylated interferon-alpha, three nucleoside analogs (lamivudine, entecavir and telbivudine) and two nucleotide analog prodrugs (adefovir dipivoxil and tenofovir disoproxil fumarate) (11). Current antiviral agents can control but not eliminate HBV because HBV establishes a stable nuclear cccDNA. These drugs have little impact upon the levels of cccDNA and, therefore, while helpful to control infection, have little effect upon long-term HBV persistence. Strategies to eliminate cccDNA may prove very helpful for treatment of hepatitis due to chronic HBV infection (12-14).

Human papillomavirus (HPV) is a small double-stranded DNA virus that colonizes various stratified epithelia like skin, oral and genital mucosa, and induces the formation of self-limiting benign tumors known as papillomas (warts) or condylomas. Most of these benign tumors naturally regress due to the influence of host immunological defenses. Some HPVs, however, have oncogenic potential and have been associated with certain types of cancers. See, Lorincz et al., Obstetrics & Gynecology, 79:328-337 (1992); Beaudenon et al., Nature, 321:246-249 (1986); and Holloway et al., Gynecol. One., 41:123-128 (1991).

HPV is the most prevalent, sexually transmitted virus. More than 35 HPV genotypes are known to be sexually transmitted, but a subset accounts for the majority of anogenital infections. Among these most common HPV types are two forms with high risk for carcinogenic progression (HPV16 and HPV18), and two forms that cause the majority of genital warts (HPV6 and HPV11).

An estimated 5.5 million people become infected with HPV each year in the United States, and an estimated 20 million Americans are currently infected (Cates and et al., Lancet, 354, Suppl. SIV62, 1999). Approximately 75 percent of the male and female reproductive-age population has been infected with sexually transmitted HPV and, though the main public health risk to women is cervical cancer (Koutsky, Am. J. Med., 102(5A), 3-8, 1997), genital warts constitute an epidemic. Thus, millions of people in the U.S. alone require treatment each year. It is important to note that PAP smears represent the largest public health screening program in the world, and that the test is, essentially, a measure of HPV infection. One standard for managing a positive PAP smear is "follow up". In general, no treatment is recommended unless an advanced stage of cervical dysplasia is observed (CDC Sexually Transmitted Diseases Treatment Guidelines, 2002).

Significant need exists in HPV positive subjects for effective HPV antiviral drugs. At present, no specific treatments exist for HPV or warts. Aldara™ (Imiquimod), an immunomodulator used for treating external genital warts, is the most successful treatment on the market. An effective, specific HPV treatment has the potential to significantly improve upon, and effectively compete with, Imiquimod.

The majority of human cervical carcinomas (95%) contain and express HPV DNA and it is the expression of two viral oncoproteins, E6 and E7 that appears to be critical for cellular transformation and maintenance of the transformed state. Specifically, four HPV types (HPV-16, HPV-18, HPV-31, and HPV-45) have been connected to 75-93% of the cases of cervical cancer in the United States. It has been estimated that perhaps twenty percent (20%) of all cancer deaths in women worldwide are from cancers that are associated with HPV.

HPV also causes anal cancer, with about 85 percent of all cases caused by HPV-16. HPV types 16 and 18 have also been found to cause close to half of vaginal, vulvar, and penile cancers.

Most recently, HPV infections have been found to cause cancer of the oropharynx, which is the middle part of the throat including the soft palate, the base of the tongue, and the tonsils. In the United States, more than half of the cancers diagnosed in the oropharynx are linked to HPV-16.

HPVs can be further classified as either high or low risk based on the clinical lesions with which they are associated or the relative propensity for these lesions to progress to cancer. Low risk cutaneous types, such as HPV types HPV-1, HPV-2, HPV-3, HPV-4, HPV-5, HPV-7, HPV-8, and HPV-9 cause common warts (verrucae vulgaris), plantar warts (verrucae plantaris), mosaic warts, flat warts (verrucae plane), and butcher warts. Furthermore, HPV types HPV-6 and HPV-11 cause warts of the external genitalia, anus and cervix. High-risk types, such as HPV-16, HPV-18, HPV-31, HPV-33 and HPV45 are particularly common in intraepithelial carcinomas, neoplasias and cancers. In particular, the genomes of two HPV types, HPV-16 and HPV-18, have been found to be associated with about 70 invasive carcinomas of the uterine cervix, as well as cancers of the oro-pharynx, anus, and other mucosal tissues.

Current treatment for HPV infection is extremely limited. Management normally involves physical destruction of the wart by surgical, cryosurgical, chemical, or laser removal of infected tissue. Some of these current treatments, like laser removal and surgery, are expensive and require the use of anesthesia to numb the area to be treated. Cryosurgical removal requires the use of special equipment. Furthermore, most subjects experience moderate pain during and after the procedure.

Topical creams and solutions such as preparations of 5-fluorouracil, Imiquimod, cidofovir, formaldehyde, glutaral, cimetidine, tricholoroacetic acid, bleomycin, podofilox and podophyllum preparations have also been used. (Reichman in Harrison's 7 Principles of Internal Medicine, 13th Ed. (Isselbacher et al., eds.); McGraw-Hill, Inc., NY (1993) pp. 801-803). Recurrence after these treatments, however, is common, most likely because the virus remains latent within the host epithelial cells. Therefore, subsequent repetitive treatments must be used, which can destroy healthy tissue. These treatments are not available or approved for treatment of cervical infections.

Interferon has also been employed as a treatment for persistent HPV infections and warts. However, its effectiveness is limited. Chang et al. (2002) Journal of Virology 76: 8864-74, found some cells infected with HPV genomes became resistant to interferon treatment after only a few applications. See also Cowsert (1994) Intervirol. 37:226-230; Bornstein et al. (1993) Obstetrics Gynecol. Sur. 4504: 252-260; Browder et al. (1992) Ann. Pharmacother. 26:42-45.

Thus, there is a need for therapeutics for treating a number of diseases and conditions as outlined herein.

BRIEF SUMMARY OF THE INVENTION

The present invention provides compounds and methods for treating subjects who have been infected with a double-stranded DNA virus, for example, human papillomavirus or polyomavirus. The polyamide compounds of the invention are useful as treatments for papillomavirus or polyomavirus related diseases. In some embodiments, the polyamide antiviral agents are well suited for treating PyVAN, hemorrhagic cystitis and PML. In some embodiments, the polyamide antiviral agents are well suited for treating cervical epithelia and anal epithelia, conjunctiva papillomas, condyloma accumulata and recurrent respiratory papillomatosis (RRP).

Chemical compositions known as polyamides, and their formulations for cell culture, tissue culture and use against high-risk human papillomavirus (HPV16, 18 and 31), are described in U.S. Patent Application Publication No. 2009/0306164, U.S. Patent Application Publication No. 2013/0090362, as well as U.S. Pat. No. 7,589,171, U.S. Pat. No. 8,119,677 and U.S. Pat. No. 8,993,609. These polyamide compounds, compositions and formulations are herein incorporated by reference to the aforementioned disclosures in their entirety.

The present invention provides polyamides, polyamide compositions, and analogs or derivatives thereof, and methods for treating polyomavirus infected cells and methods for treating papillomavirus infected cells by administering the polyamides of the invention.

The present invention provides a method of treating polyomavirus or papillomavirus infections, including infected subjects, cells, organs tissues, and the like, referred to hereafter as infected entities, comprising contacting the infected entities according to a manner described here, or using a related treatment common to pharmaceutical and biological practice.

In an embodiment, the invention provides a method of treating human papillomavirus or polyomavirus infected entities comprising administering to a patient or subject a polyamide compound or pharmaceutical composition comprising a polyamide compound described herein. In an aspect of the invention, the method further comprises contacting the infected entities with an anti-viral agent in addition to the polyamide compound.

In an embodiment, the polyomavirus may be selected from SV40, BKV, JCV, KI polyomavirus, MCPyV, WU polyomavirus or polyomavirus 9.

In another aspect, the HPV may be selected from HPV1, HPV6, HPV11, HPV16, HPV18, HPV31, HPV33, HPV35, HPV39, HPV45, HPV51, HPV52, HPV56, HPV58, HPV59, HPV66 or HPV68.

The present invention further provides a method of treating virus infected cells comprising contacting the cells with an effective amount of a polyamide in accordance with the invention. The virus may be selected from HPV, polyomaviruses, or other double-stranded DNA viruses. A subject infected with HPV may be treated by a method, which comprises administering to the subject an effective amount of a polyamide having a structure as described herein. The polyamide compound may be administered in the form of a pharmaceutical composition comprising the compound and a pharmaceutically acceptable carrier. In other embodiments, the invention provides a method of treating double-stranded DNA virus infected cells comprising administering to a patient a compound selected from the classes described herein.

Examples of polyamide compounds are generically and specifically described herein.

In an embodiment, the invention provides a method of treating a subject exhibiting or who is suspected of exhibiting HPV infected cells or polyomavirus infected cells by administering to the subject a compound selected from compounds listed in Table 1.

In an embodiment, the method further comprises administering antiviral agents selected from cidofovir, CMX-001, leflunomide, adefovir, entecavir, lamivudine, telbivudine, tenofovir, interferon, pegylated interferon, and/or drugs effective against hepatitis B, in combination with the polyamides of the invention for the treatment of subjects/patients exhibiting or suspected of exhibiting a HPV, polyomavirus infection and/or other infections caused by double-stranded DNA viruses.

The methods of this invention exhibit efficacy against papillomavirus or polyomavirus related disease, or both, that is superior to other available antiviral treatments. This superior efficacy is due to the ability of the polyamide compounds to trigger elimination of DNA viral episomes. The polyamides are known to bind viral DNA directly, and this may be part of the trigger. The diseases benefiting from treatment include prevention of HPV-derived cancers and direct HPV infections, as well as polyomavirus related diseases including PML, PyVAN, hemorrhagic cystitis, and Merkel cell carcinoma.

Moreover, the HPV related diseases benefiting from treatment include genital or cutaneous warts, HPV infections of oral or genital tissues including cervical epithelia and anal epithelia caused by the HPV, conjunctiva papillomas, condyloma accumulata and recurrent respiratory papillomatosis (RRP).

In some embodiments, polyamide sequences exhibiting anti-HPV activity with the HPV types, especially, HPV 1, 6, 11, 16, 18 and 31, display the ability to displace or eliminate HPV DNA from host chromosomes, which can result in broad applicability against HPVs. These include HPV11, which is responsible, in part, for the frequently fatal disease known as respiratory papillomatosis, as well as genital warts, HPV1 and 6, which cause common warts and warts of the external genitalia, anus and cervix, respectively, and HPV16, 18 and 31, which are responsible for anal and/or cervical cancers.

Notwithstanding the foregoing, it may nonetheless not be predicted which double-stranded DNA (dsDNA) viruses are suitable targets for treatment with a therapeutically effective amount of the pharmaceutical compositions comprising the polyamides of the invention.

What we therefore believe to be comprised by our invention may be summarized inter alia in the following words.

A compound of the formula:
Guan-PPPβPPPβPIm-γ-PβPPβPPPβPPβTa;
TMG-PPβPPPβPIm-$γ_{NH2}$-PβPPβPPPβPPTa;
Guan-PPPβPPPβPIm-γ-PβPPβPPPβPβDp;
TMG-PPPβImβPPP-γ-PPβPPPβPPPβTa;
TMG-PPPβPPPβPIm-$γ_{NHR}$-PβPPβPPPβPβTa;
ImPPβPPImβPP-γ-PPβPPPβPPPβTa;
TMG-PPβPPImβPP-γ-PPβPPPβPPPβTa;
TMG-PPPβPPβPIm-γ-PβPPβPPPβPβDp;
TMG-PPPβPPβPIm-γ-PβPPβPPPβPβTa;
Guan-PPβPImβPP-γ-PPβPPPβPPPβPβTa;
TMG-PPPβPPβP-γ-PPPβPPPβPβ-TA;
ImPPβPPImβPP-γ-PPβPPPβPPPPTa;
TMG-PPPβPPβPIm-$γ_{NH2}$-PβPPβPPPβPβTa
TMG-PPβPPβP-γ-PPPβPPPβPβTa;
Guan-IPPβPPIβPP-γ-PPβPPPβPPPβTa;
TMG-IPPβPPIβPP-γ-PPβPPPβPPPβTa;
ImPPβPPIMβPP-γ-PPβPPPβPPPβDp;
TMG-PPβPPPImβPP-γ-PPβPPPβPPPβDp;
TMG-PPPβPPbP-$γ_{NHR}$-PPβPPPβPPPβDP;
ImPPβPPPImβP-γ-PPβPPPβPPPβTa;
ImPPβPPImβPP-$γ_{NH2}$-PPβPPPβPPPβtga;
TMG-PβPPImβPP-γ-PPβPPPβPPPβDp;
Guan-PPβPPUmβPP-γ-PPβPPPβPPPβDp;
Guan-IPPβPPP-γ-PPβPPPPβTa;
ImPPβPPP-γ-PPβPPPPβTa;
TMG-IPPβPPP-γ-PPβPPPPβTa;
ImPPβPP-γ-PPβPPPPβTa;
ImPPβPPP-$γ_{NH2}$-PPβPPPPβTa;
ImPPβPPImβPP-$γ_{NHAc}$-PPβPPPβPPPβDp;
Guan-PPβPPP-γ-PPβPPPPβTa;
ImPPβPPPβ-γ-PPβPPPβPPDp;
TMG-PPβPPP-γ-PPβPPPPβTa; or
Guan-PPβPPP-γ-PPβPPPPβ3Dp,
wherein GUAN=a guanidinyl radical; TMG=tetramethylguanidinyl;
P=4-amino-2-carbonyl-N-methylpyrrole; γ=gamma-aminobutyric acid;
$γ_{NH2}$=(R)-2,4-diaminobutyric acid reacted through either the 2-amino group or the 4-amino group; $γ_{NHAc}$=(R)-2-(acetylamino)-4-aminobutyric acid;
β=beta-alanine; Im=4-amino-2-carbonyl-N-methylimidazole;
Ta=3,3'-diamino-N-methyldipropylamine; and Dp=(dimethylamino)propylamine, such a
compound which is in the form of a formate salt, such a
use of a compound in a medicament for the treatment of polyomavirus infected cells, such a
method of treating cells infected with a polyomavirus comprising administering to a subject infected with the polyomavirus, a therapeutically effective amount of a compound, such a
compound of the formula:
ImPPPPβPP-γ-PPPβPPPβDp;
ImPPPPβPPβPPP-$γ_{NH2}$-PPPPβPPPβPPPPβDp;
ImPPPPβPPβPPP-γ-PPPβPPPβPPPβDp;
ImPPPPβPPP-$γ_{NH2}$-PPPβPPPβPβDp;
ImPPPPβPPβ-γ-PPβPPPβPβTa;
ImPPPβPPP-γ-PPβPPPPβTa;
ImPPPPβPPβ-$γ_{NH2}$-PPβPPPβPβDp;
ImPPβPPP-$γ_{NH2}$-PPβPPPPPβTa;
ImPPPPβPPP-γ-PPPβPPPβPβTa;
ImPPPPβPPβ-$γ_{NH2}$-PPβPPPβPβTa;
ImPPβPImβPP-$γ_{NH2}$-PPβPPPβPPPβTa;
ImPPβPPImβPP-γ-PPβPPPβPPPPβDp;
ImPPβPPImβPP-γ-PPβPPPβPPPPβTa;
ImPPPPIm-γ-βPPPPβDp;
ImPPPPIm-γ-βPPPPβTa;
ImPPβPImβPPIm-γ-βPβPPPβPPPβTa;
ImPβPPPβPPImβPPP-γ-PβPPβPPPβPPPPβTa;
ImPPPPβPPβPP-γ-PPPβPPPβPPPβDp;
ImPPPPβPPβPP-γ-PPPβPPPβPPPβTa;
ImPPβPPImβPPαPPβPPPβPPPβTa (5 TFA);
ImPPβPPImβPPαNH2PPβPPPβPPPβDp (4 TFA);
ImPPβPPImβPPαNHAcPPβPPPβPPPβTa (4 TFA);
ImPPPImαNH2βPPPPβTa (5 TFA);
ImPPβPPmPP-NHcPP3PPPβTa (3 TFA);

ImPPβPPImβPP-γ$_{NH2}$-PPβPPPβPPPβDp;
ImPPβPPImβPP-γ$_{NH2}$-PPβPPPβPPPβTa;
ImPPβPPImβPP-γ$_{NHc}$-PPβPPPβPPPβDp;
ImPPβPPP-γ-PPβPPPPTa.3TFA;
ImPPβPImβPP-γ-PPβPPPβPPPPTa.4TFA;
TMG-PPβPPβPIm-γ$_{NH2}$-PβPPβPPPβPPTa.5TFA;
TMG-PPPβPPβPIm-γ$_{NHR}$-PβPPβPPPβPβTa.6TFA;
TMG-PPPβPPβPIm-γ$_{NH2}$-PβPPβPPPβPβTa.5TFA;
TMG-PPPβPPβP-γ$_{NHR}$-PPPβPPPPβPβTa.5TFA;
TMG-PPPβPPβPIm-γ$_{NH2}$-PβPPβPPPβDp.4TFA;
TMG-PPPβPPβP-γ$_{NH2}$-PPPβPPPβPPβPβTa;
TMG-PPPβPPβP-γ$_{NH2}$-PPPβPPPβPPβPβDp;
TMG-PβPPImβPP-γ-PPβPPPβPPPβTa.4TFA;
TMG-PPPβPPβP-γ$_{NHR}$-PPPβPPPβPβDp.3TFA;
TMG-PβPPImβPP-γ-PPβPPPβPPPβDp.3TFA;
TMG-PPβPPP-γ-PPβPPPPβDp.2TFA;
TMG-PPβPPP-γ-PPβPPPPβTa.3TFA;
TMG-PPβPPImβPP-γ-PPβPPPβPPPβTa;
TMG-PPβPPImβPP-γ-PPβPPPβPPPβDp;
TMG-PPβPPImβPP-γ-PβPPβPPPβPβTa;
TMG-PPβPPImβPP-γ-PβPPβPPPβPβDp;
TMG-PpβPPβPIm-γ-PβPPβPPPβPβPβDp;
TMG-PpβPPβPIm-γ-PβPPβPPPβPβTa;
ImPPβPP-γ-PPβPPPPβTa;
ImPPβPPImβP-γ-PPβPPPβPPPβTa;
TMG-PPβPPβP-γ$_{NH2}$-PPPβPPPβPβTa;
TMG-PpβPPβPIm-γ$_{NH2}$-PβPPβPPPβPβTa;
TMG-PPβPPβP-γ-PPPβPPPβPβ-Ta.3TFA;
TMG-PPPβPPβP-γ-PPPβPPPβPβ-Ta.3TFA;
Guan-PPβPPImβPP-γ-PPβPPPβPPPβTa (4 TFA);
Guan-PPβPPP-γ-PPβPPPPβTa (3 TFA);
Guan-PPβPPImβPP-γ-PPβPPPβPPPβDp (3 TFA);
Guan-PPβPPP-γ-PPβPPPPβDp (2 TFA);
Guan-PPPβPPβPIm-γ-PβPPβPPPβPβTa (4 TFA);
Guan-PPPβPPβPIm-γ-PβPPβPPPβPβDp (3 TFA);
TMG-IPPβPPP-γ-PPβPPPPβTa (4 TFA);
TMG-IPPβPPIβPP-γ-PPβPPPβPPPβTa (5 TFA);
Guan-IPPβPPP-γ-PPβPPPPβTa (4 TFA);
Guan-IPPβPPIβPP-γ-PPβPPPβPPPβTa (5 TFA);
Ac-IPPβPPIβPP-γ-PPβPPPβPPPβTa (5 TFA);
PPβPPβPIm-γ-PβPPβPPPβPβTa;
ImPPPβPP-γ-PPβPPPPβTa (3 HCO2H);
ImPPPβPP-γ-PPPβPPPPβTa (3 HCO2H);
TMG-ImPβPPP-γ-PβPPPPβTa (4 HCO2H);
Guan-ImPβPPP-γ-PβPPPPβTa (4 HCO2H);
ImPβPPP-γ-PβPPPPβTa (3 HCO2H);
ImPPβPP-γ-PPβPPPPβTa (3 HCO2H);
TMG-ImPβPPP-γ-PPβPPPPβTa (4 HCO2H);
Guan-ImPβPPP-γ-PPβPPPPβTa (4 HCO2H);
TMG-PPImβPP-γ-PPβPPPPβTa (4 HCO2H);
Guan-PPImβPP-γ-PPβPPPPβTa (4 HCO2H);
PPImβPP-γ-PPβPPPPβTa (3 HCO2H);
ImPPβPPImβPP-γ-PPβPPPβPPPβTa (4 HCO2H);
ImPPPβPP-γ-PPPβPPPPβDp (2 TFA);
ImPPβPPImβPP-γ-PPβPPPβPPPβTa-AF488; or
ImImPIm-γ-PβPPPβTa-AF488 (2 HCO$_2$H),
wherein GUAN=a guanidinyl radical; TMG=tetramethylguanidinyl; P=4-amino-2-carbonyl-N-methylpyrrole; γ=gamma-aminobutyric acid; γ$_{NH2}$=(R)-2,4-diaminobutyric acid reacted through either the 2-amino group or the 4-amino group; γ$_{NHAc}$=(R)-2-(acetylamino)-4-aminobutyric acid; β=beta-alanine; Im=4-amino-2-carbonyl-N-methylimidazole; Ta=3,3'-diamino-N-methyldipropylamine; Dp=(dimethylamino)propylamine; TFA=trifluoroacetic acid; HCO2H=formate; a means that the γ-aminobutyric acid formed an α-linked hairpin rather than the typical γ-linked hairpin; and AF488=AlexaFluor-488 fluorophore, such a compound which is in the form of a formate salt, such a
use of a compound in a medicament for the treatment of papillomavirus infected cells, such a
method of treating cells infected with a papillomavirus comprising administering to a subject infected with the papillomavirus, a therapeutically effective amount of the compound.

BRIEF DESCRIPTION OF THE FIGURES

FIG. 9.

DETAILED DESCRIPTION OF THE INVENTION

Figure 1:
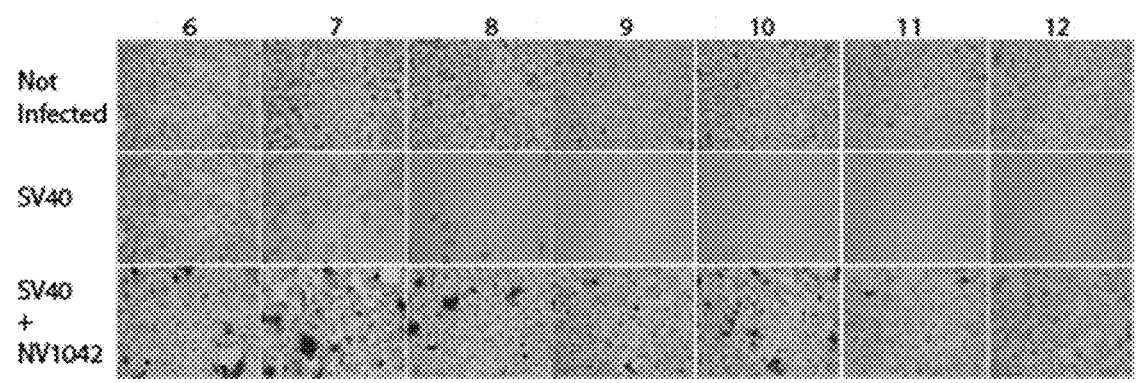
FIG. 1: Light micrographs of Giemsa stained, adherent BSC-1 cells following infection with SV40 and following SV40 treatment and treatment with 10 μM NV1042 at day 1 post-infection. Note that NV1042 cells are protected from SV40 infection.
Figure 2:
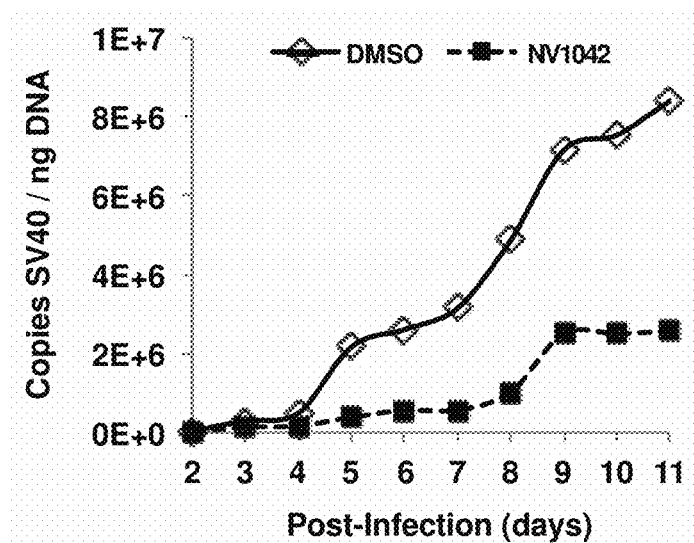
FIG. 2: Viral copies of SV40 per ng of DNA in adherent and floating cells in SV40 cells infected with SV40 (MOI=1) or in infected cells treated with and single, 48 hour dose of 10 μM NV1042 delivered on day 2 post-infection. Copies of SV40/ng DNA are plotted on an exponential scale.
Figure 3:
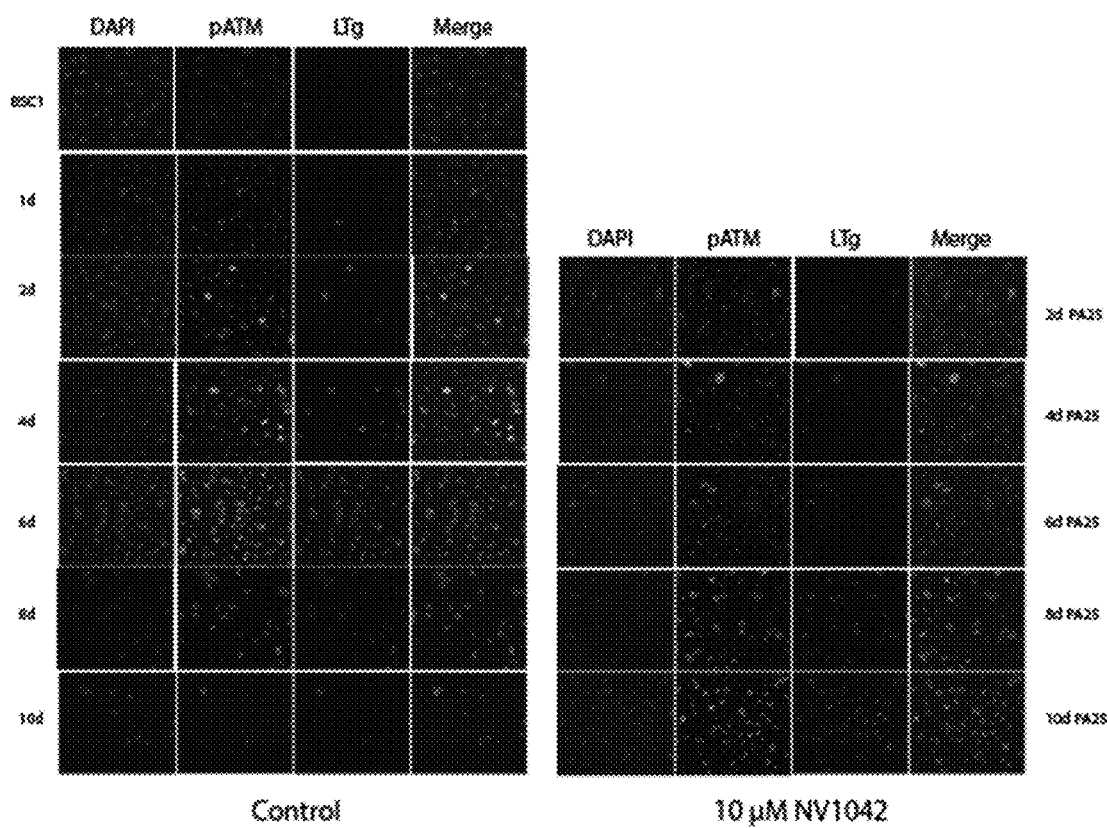
FIG. 3: Time course as in FIG. 1 showing expression of large T antigen (LT or LgT-ag, red) and appearance of activated phospho-ATM (pATM, green) in days post SV40 infection in BSC-1 cells that have received no compounds or been treated at day 1 post infection with NV1042. DAPI stained nuclei are in blue. Cells were infected with a multiplicity of infection (MOI)=1.
Figure 4:
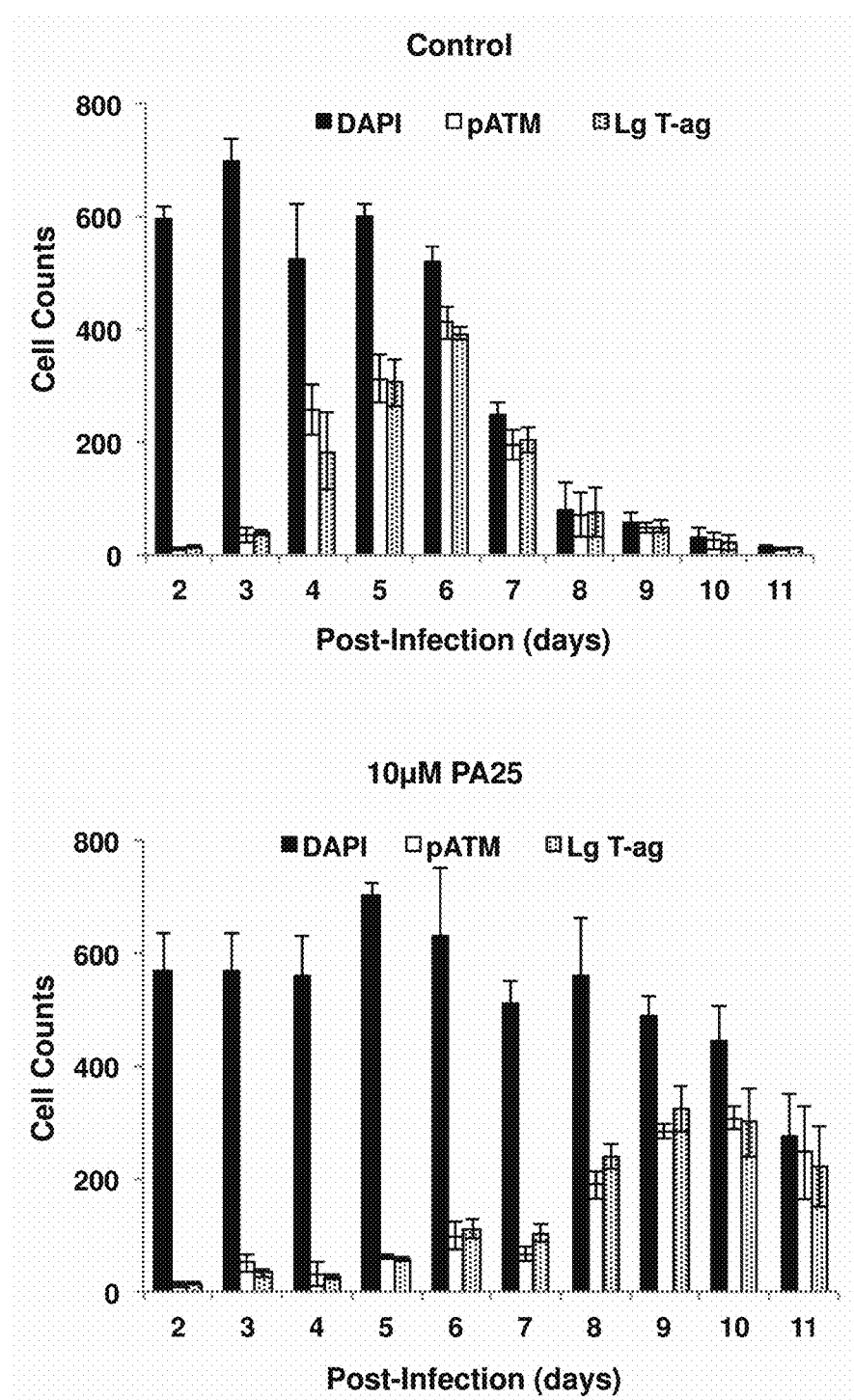
FIG. 4: Quantification of levels of total cells, pATM positive cells, and LTag cells from time course illustrated in FIG. 3. Cells were infected with a multiplicity of infection (MOI)=1.
Figure 5:
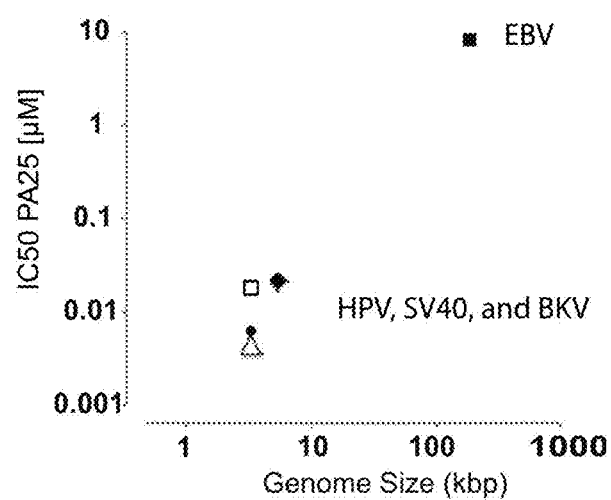
FIG. 5: The size of the DNA virus episome appears to correlate with polyamide activity. HPV16, SV40, and BKV-Tu and BKV-Dun strains all exhibit similar IC$_{50}$'s in response to NV1042 in the low nm range. The results indicate that NV1042 is practical for treating the small DNA viruses HPV, SV40, and BKV.

The present invention provides compounds and methods for treating infections caused by double-stranded DNA viruses and other diseases in subjects/patients by administering polyamides and analogs of polyamide polymers.

For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

The polyamides of the present invention may be generally described as polymeric or oligomeric molecules containing a plurality of carboxamide repeating units such as those represented in the figure and, optionally, at least one guanidinyl radical per molecule.

Polyamides may be produced from known starting materials by known methods. See for example WO 05/033282, Belitsky et al., (2002) Bioorg. Med. Chem., 10, 2767-74; Zhang, et al. (2006) J. Am. Chem. Soc. 128:8766-76; Turner, et al. (2001) Organic Letters, 3:1201-03. Polyamides can be prepared using manual solid-phase synthesis as well as automated solid-phase chemistry. Each coupling is followed by HPLC and HPLC/mass spectrometry (HPLC/MS). Electrospray ionization and analysis of multiply-charged ions has allowed HPLC/MS to work effectively with a single quadrupole detector, but more sophisticated instruments are used for high resolution mass spectrometry (HRMS).

The polyamide compounds of the invention are made by standard solid phase Boc methods (Baird, E. E.; Dervan, P. B. *J. Am. Chem. Soc.* 1996, 118, 6141) with Boc-8-PAM resin from Peptides International. However, the chemistry is altered to improve yields and purity as follows: PyBOP (benzotriazol-1-yl-oxy-tripyrrolidinophosphonium hexafluorophosphate) is used as the coupling agent and extensive use is made of dimer building blocks to cut down the number of solid phase steps and to eliminate some byproducts. Purification is by reverse phase HPLC with 0.1% trifluoroacetic acid in the aqueous phase, except when formate salts are to be isolated, in which case formic acid is used in the aqueous mobile phase. Regarding stoichiometry, the highly basic TMG and Guan groups are always protonated upon isolation, as are all weakly to moderately basic nitrogens, given the acidity of the mobile phase.

With regard to chemical background, certain oligomers of nitrogen heterocycles can be used to bind to particular regions of double stranded DNA. Particularly, N-methyl imidazole (I), des-amino-N-methyl imidazole (Im), and N-methyl pyrrole (P) have a specific affinity for particular bases. This specificity can be modified based upon the order in which these compounds are linked. It has been shown that there is specificity in that G/C is complemented by Im/P or I/P, C/G is complemented by P/Im or P/I, and A/T and T/A are redundantly complemented by P/P.

In effect, N-methyl imidazole and des-amino-N-methyl imidazole tend to be associated with guanine, while N-methyl pyrrole is associated with cytosine, adenine and thymine. By providing for two chains of the heterocycles, as 1 or 2 molecules, a 2:1 complex with double stranded DNA is formed, with the two chains; of the oligomer antiparallel, where G/C pairs have Im/P or I/P in juxtaposition, C/G pairs have P/Im or P/I, and T/A pairs have P/P in juxtaposition. The heterocycle oligomers are joined by amide (carbamyl) groups, where the NH may participate in hydrogen bonding with nitrogen unpaired electrons, particularly of adenine.

Polyamides may be synthesized to form hairpin compounds by incorporating compounds, such as gamma-aminobutyric acid (γ or -γ-) or gamma-2,4-diaminobutyric acid ($γ_{NH2}$ or $-γ_{NH2}$-), usually in the (R) form, to allow a single polyamide to form a complex with DNA.

Beta-alanine (β) may be substituted for a pair of N-methyl pyrrole groups when an AT or TA base pair is the target sequence. The added flexibility of the beta-alanine can help the entire polyamide stay "in register" with the target sequence of DNA.

In some embodiments, the polyamide molecule begins with des-amino-N-methyl imidazole which has a specific affinity for guanosine. In other embodiments, the polyamide molecule ends with either 3-(Dimethylamino) propylamine (Da) or 3,3'-Diamino-N-methyldipropylamine (Ta). Dye molecules can be incorporated at the amino groups of the γ-amino-butyric acid, the Ta, or at both of these sites if both are available in the same molecule.

The polyamide building blocks are shown as radicals present in a polyamide chain rather than as free amino acid molecules or N-protected amino acids prior to their coupling into a polyamide. Pyrrole (Structure I below, typically abbreviated Py or P) binds to the three nucleotides that present hydrogen bond acceptors in the minor groove, or A, T and C (21, 22). These nucleotides present only hydrogen bond acceptors to the minor groove: A and C each offer one lone pair of electrons while T offers two lone pairs from the carbonyl oxygen bound to C2. It is the amide NH of the hairpin pyrrole amino acids that is the hydrogen bond donor. So, the pyrrole ring acts as a curved spacer that presents amide NHs at the correct distance and curvature to match up with the pattern of hydrogen bond acceptors presented by A, C and T when located in B-form DNA. Imidazole (Structure II below) is typically abbreviated I or Im.

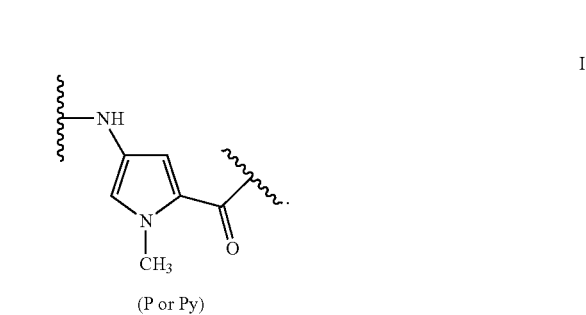

(P or Py)

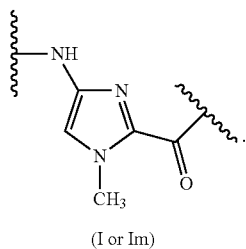

(I or Im)

Additional polyamide building blocks and binding rules can be found in the art (16, 23). However, these studies showed that β-alanine (Structure III (β), below) can act as an H-bond donor that is selective for A, T and C.

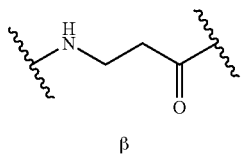

β

For additional recognition, the γ-amino butyric acid (Structure IV (γ) below) building block used to form the hairpin turn was originally reported to bind NT or TA, but not G/C or C/G base pairs. Similar preference for A/T over G/C base pairs is reported for the positively-charged amino tail that is present in most polyamides. This mimics the cationic group in distamycin (16, 19, 23-26). Standard hairpin polyamides often show the highest affinity for sequences that begin 5'-WWG-3', where W=A or T.

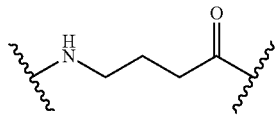

Other building blocks include, without limitation, desamino-imidazole (Formula V (Im)), (R)-2,4-diaminobutyric acid (Formula VI, γNH$_2$), the N-acetyl version of formula VI (γ$_{NHAc}$ or -γ$_{NHAc}$—, not shown), 3-(dimethylamino)propylamine (Formula VII, Dp) and 3,3'-diamino-N-methyl-dipropylamine (formula VIII, Ta).

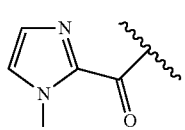

(Im, dIm or desIm)

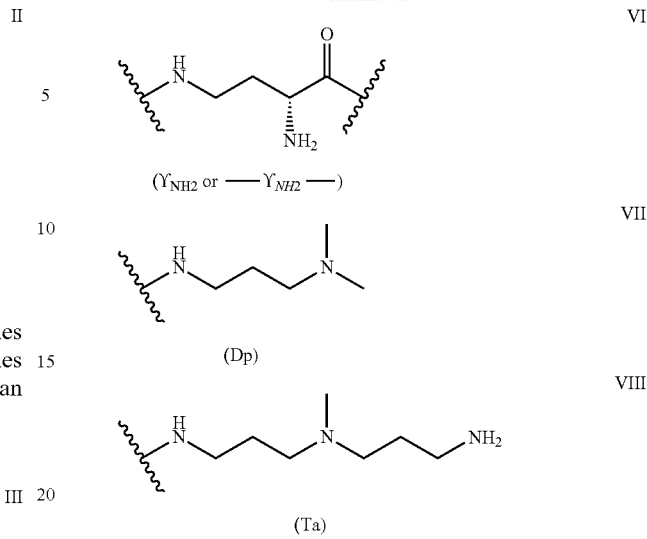

New N-termini for polyamides that show high efficacy are the tetramethylguanidinyl (Structure IX) and unsubstituted guanidinyl (Structure X) groups, where structure X occurs in a number of tautomeric forms:

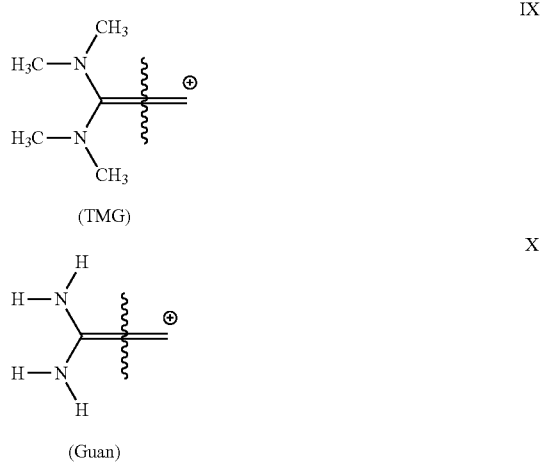

The polyamides of the present invention may be generally described as polymeric or oligomeric molecules containing a plurality of carboxamide repeating units and at least one guanidinyl radical per molecule. In one embodiment, the polyamide is a compound having a polyamide backbone containing an interior unit selected from γ-aminobutyric acid (γ); 2,4-diaminobutyric acid (γ$_{NH2}$), which may be either the (R) or (S) isomer and which may be linked in to the backbone of the polyamide through either the 2-amino group (to form an alpha turn) or through the 4-amino group (to form a gamma turn); or H$_2$N(CH$_2$)$_2$CH(NHC(=O)NHR)CO$_2$H (either the (R) or (S) isomer), wherein R is —(CH$_2$)$_3$—N(CH$_3$)—(CH$_2$)$_3$—NH$_2$ (γ$_{NHR'}$) or —(CH$_2$)$_3$—N(CH$_3$)$_2$ (γ$_{NHR''}$), and at least one guanidinyl radical pendant to 2,4-diaminobutyric acid (γ$_{NH2}$), and/or pendant to H$_2$N(CH$_2$)$_2$CH(NHC(=O)NHR)CO$_2$H, wherein R is —(CH$_2$)$_3$—N(CH$_3$)—(CH$_2$)$_3$—NH$_2$ (γ$_{NHR'}$), and/or at a terminal position of the polyamide backbone. The compound may be a pharmaceutically acceptable salt of such a polyamide. In the context of this invention, "interior" means at a position along the polymer backbone other than the terminal (end) positions or immediately adjacent to the terminal positions. The polyamide backbone may, in addition to the aforementioned interior unit, contain a plurality of units (for example, 5 to 30, or 7 to 28, or 9 to 24, or 11 to 22 or 15 to 21 or 16 to 21 units) selected from the group consisting of 4-amino-2-carbonyl-N-methylimidazole (Im), 4-amino-2-carbonyl-N-methylpyrrole (Py) and β-alanine (B).

Figure 9A:
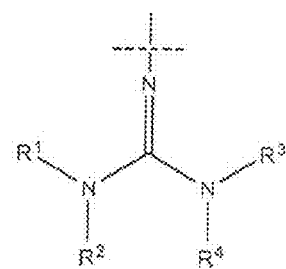
FIGS. 9A and 9B illustrate various types of guanidinyl radicals, including different substitution patterns and tautomers, which may be present in the polyamides of the present invention.
Figure 9A:
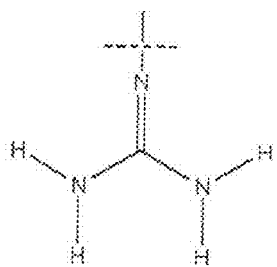
Figure 9A:
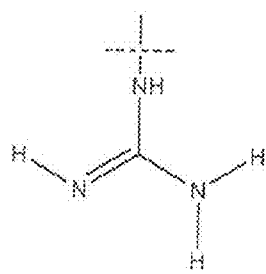
Figure 9A:
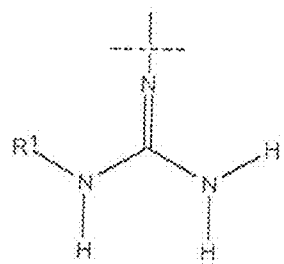
Figure 9A:
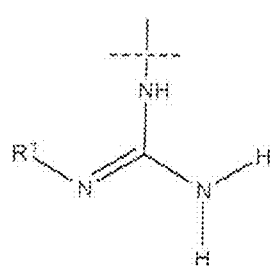
Figure 9A:
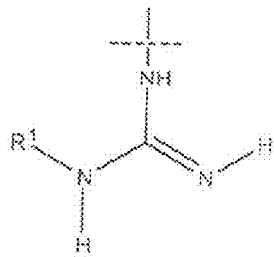
Figure 9A:
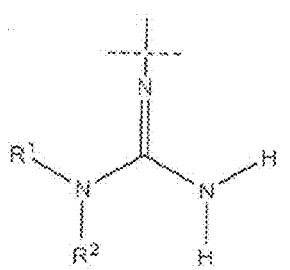
Figure 9A:
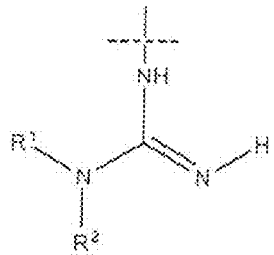
Figure 9B:
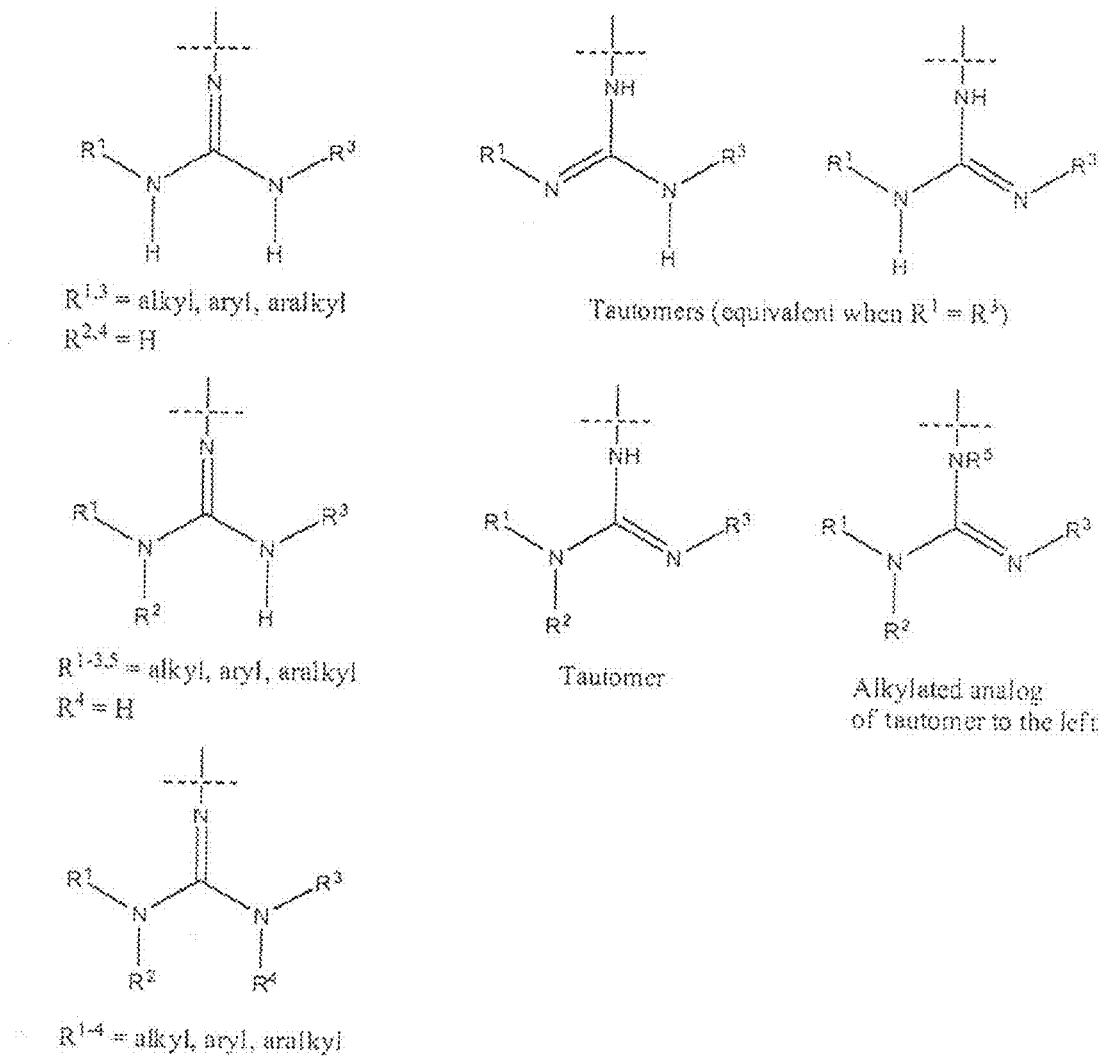

In other aspects of the invention, the guanidinyl radical may be unsubstituted or substituted. That is, the three nitrogen atoms present in the guanidinyl radical may bear substituents other than hydrogen. Such substituents may be, for example, alkyl, aralkyl and/or aryl groups. Examples of these variously substituted guanidinyl radicals and their related tautomers are shown in FIGS. 9A and 9B. In one embodiment of the invention, two of the nitrogen atoms each bear two alkyl groups, such as C1-C4 alkyl groups. For example, the guanidinyl radical may be tetramethylguanidinyl (TMG, IX).

In one aspect of the invention, the guanidinyl radical is connected to a terminal 4-amino-2-carbonyl-N-methylpyrrole (Py) unit (i.e., the primary amine group initially present in the Py unit becomes part of the guanidinyl radical). In another aspect of the invention, a des-aminoimidazole (des-Im) forms the amino-terminus of the molecule and a guanidinyl radical is attached to an amino group elsewhere in the molecule, on for example the Ta or γ-$_{NH2}$ group.

The compound may contain a C terminus end group selected from 3,3'-diamino-N-methyldipropylamine (Ta) or 3-(dimethylamino)propylamine (Dp).

Compounds and formulations for treating PyV and/or HPV infections are described herein. According to this invention an "effective amount" of the compound or pharmaceutically acceptable composition is that amount effective for treating or lessening the severity of PyV and/or HPV infections.

If other indications are being treated with the polyamides described here, then an "effective amount" would be defined as per the norms of treatment for those diseases.

The method of treating PyV and/or HPV infections comprises administering a pharmaceutical composition comprising a polyamide of the invention.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

The pharmaceutical compositions, according to the method of the present invention, may be administered using any amount and any route of administration effective for treating or lessening the severity of PyV and HPV related disease. Ex-vivo organ or tissue such as kidney or bone marrow, treated with active polyamide prior to transplant surgery, can eliminate the reservoir of PyV and/or HPV (e.g., even if HPV is undetected in the ex-vivo organ or tissue, this is a possible precautionary measure to remove any HPV reservoir).

The invention relates to treating PyV or HPV infected entities including PyV or HPV in a biological sample or a patient (e.g., in vitro or in vivo), which method comprises administering to the patient (human or other animal), or contacting said biological sample with a pharmaceutical composition comprising a polyamide as described herein. The term "biological sample", as used herein, includes, without limitation, cell cultures or extracts thereof; biopsied material obtained from a mammal or extracts thereof; and blood, saliva, urine, feces, semen, tears, or other body fluids or extracts thereof. The term "patient" includes animals, including mammals, humans, primates, dogs, cats, horses, pigs, cows, sheep and the like.

After the cells of an individual become exposed and infected with a PyV or HPV, a number of viral episome copies may become established within an infected cell. The PyV or HPV episomes further replicate as the cells divide. Polyamides designed to target A/T-rich regions of DNA efficaciously promote the clearance of viral episomes in the cases described before (HPV16, 18, 31). Efficacy is determined experimentally on a case by case basis. The methods of the present invention can be used beneficially as a therapeutic method to treat PyV or HPV infections.

The polyamides used to treat PyV or HPV include, without limitation, those described herein. In an aspect, the virus may be a PyV such as BKV, McPyV, or JCV.

In an embodiment, the invention provides a method of treating PyV and/or HPV affected cells comprising contacting the cells with a compound described herein. In an aspect of the invention, the method further comprises contacting the cells with an anti-viral agent. The anti-viral agent may be an Interferon, pegylated Interferon, cidofovir, CMX-001, leflunomide, adefovir, entecavir, lamivudine, telbivudine, tenofovir, acyclovir and/or other herpesvirus/cytomegalovirus drugs.

In an embodiment, the invention provides a method of treating PyV or HPV affected cells in a patient or subject, comprising administering to a patient or subject a polyamide compound or pharmaceutical composition comprising a polyamide compound described herein.

In an embodiment, the polyamides and pharmaceutical compositions comprising polyamides used to treat double-stranded DNA virus-infected cells, for example, HPV infected cells or PyV infected cells, have the structure selected from the group of compounds listed in Table 1 and Table 3.

Polyamide oligomers may be synthesized starting with Boc-β-alanine-PAM solid phase synthesis resin, or a similar commercially available resin such as Fmoc-β-alanine-Wang resin, adding building blocks as required for the target sequence. The final step in the preparation of a guanidinylated polyamide is exemplified by incorporation of a tetramethylguanidinyl (TMG) group at the N-terminus TMG-polyamide synthesis involves placement of the tetramethylguanidinyl radical using HATU (2-(7-aza-1H-benzotriazole-1-yl)-1,1,3,3-tetramethyluronium hexafluorophosphate).

Table 1 lists a number of exemplary polyamides synthesized in accordance with the present invention. The HPLC/MW values given in Table 2 were obtained using low resolution high pressure liquid chromatography/mass spectrometry (LR HPLC/MS), which provides moderate precision masses of mixed isotopomers rather than average molecular weights or exact masses.

TABLE 1

Polyamide Compounds of the Invention

| ID | Structure |
|---|---|
| NV1002 | ImPPPβPP-γ-PPPβPPPβDp |
| NV1003 | ImPPPβPPβPPP-γ$_{NH2}$-PPPβPPPβPPPβDp |
| NV1004 | ImPPPβPPβPPP-γ-PPPβPPPβPPPβDp |
| NV1005 | ImPPPP-γ-PPPPPβTa |
| NV1006 | ImPPPP-γ$_{NH2}$-PPPPPβTa |
| NV1007*** | ImPPPP-γ-PPPPPβTa-FITC |
| NV1008*** | ImPPPP-γ-PPPPPβTa-BOFLX |
| NV1009*** | ImPPPP-γ$_{NH2}$-PPPPPβTa-FITC |
| NV1010 | ImPPPP-γ-PPPPPβDp |
| NV1011 | ImPPIm-γ-PPPPβDp |
| NV1012 | ImImImP-γ-ImPPPβDp |
| NV1013 | ImPPP-γ-PPImPβDp |
| NV1014 | ImβImP-γ-ImPPPβDp |
| NV1015 | ImβImP-γ-PPPPβDp |
| NV1016 | ImβImImP-γ-PPPPPβDp |
| NV1017 | ImPPIm-γ-PImImPβDp |
| NV1018 | ImβImPIm-γ-ImPPImPβDp |
| NV1019 | ImPPImP-γ-ImPImPPβDp |
| NV1020 | ImPPβPPP-γ$_{NH2}$-PPPβPPPβTa•4TFA |
| NV1021 | ImImPIm-γ-PImPPβDp |
| NV1022 | ImPPPβPPβ-γ-PPβPPPβPβDp |
| NV1023 | ImPPβPPP-γ-PPβPPPPβDp |
| NV1024 | ImPPβPPP-γ$_{NH2}$-PPβPPPPβDp |
| NV1025 | ImPPβPPP-γ-PPβPPPβDp |
| NV1026 | ImPPPPPP-γ$_{NH2}$-PPPβPPPβDp |
| NV1027 | ImPPβPPβ-γ-PPβPPPβPβTa |
| NV1028 | ImPPβPPP-γ-PPβPPPβPβTa |
| NV1029 | ImPPβPPβ-γ$_{NH2}$-PPβPPPβPβDp |
| NV1030 | ImPPβPPP-γ$_{NH2}$-PPβPPPPβTa |
| NV1031 | ImPPβPPP-γ-PPβPPPPβTa |
| NV1032 | ImPPPβPPβ-γ$_{NH2}$-PPPβPPPβTa |
| NV1033 | ImPPPβPPP-γ$_{NH2}$-PPPβPPPβTa |
| NV1037 | ImPPβPImPβPP-γ$_{NH2}$-PPβPPPβPPPβTa |
| NV1038 | OHC-PPPPβDp |
| NV1039 | OHC-PPPPPβDp |
| NV1040 | ImPPβPImβPP-γ-PPβPPPβPPPβDp |
| NV1041 | ImPPβPImβPPβIm-γ-βPβPPPβPPPβDp |
| NV1042 | ImPPβPImβPP-γ-PPβPPPβPPPβTa |
| NV1043 | ImPPPIm-γ-βPPPPβDp |
| NV1044 | ImPPPIm-γ-βPPPPβTa |
| NV1045 | ImPPβPImβPPβIm-γ-βPβPPPβPPPβTa |
| NV1046 | ImPβPPβPPImβPP-γ-PβPPPβPPPβPPPPβTa |
| NV1047 | ImPPPβPPPβPP-γ-PPPβPPPβPPPβDp |
| NV1048 | ImPPPβPPPβPP-γ-PPPβPPPβPPPβTa |
| NV1049 | ImPPβPImβPPαPPβPPPβPPPβTa (5 TFA) |
| NV1050 | ImPPβPImβPPα$_{NH2}$PPβPPPβPPPβDp (4 TFA) |
| NV1051** | ImPPβPImβPPα$_{NHAc}$PPβPPPβPPPβTa (4 TFA) |
| NV1052** | ImPPPImα$_{NH2}$βPPPPβTa (5 TFA) |
| NV1053** | ImPPPα$_{NHAc}$PPβPPPPβTa (3 TFA) |
| NV1054 | Ac-βPPP-γ-PPβPPPPβTa |
| NV1055 | Ac-PβPPP-γ-PPβPPPPβTa |
| NV1056 | ImPPPβPPβ-γ-PPβPPPβPPDp |
| NV1057# | ImPPβPPP-γ-PPβPPPPβdesTa (desmethyl Ta) |
| NV1058 | ImPPPIm-γ$_{NH2}$-βPPPPβTa |
| NV1059 | ImPPPIm-γ$_{NHAc}$-βPPPPβTa |
| NV1060 | ImPPPIm-γ$_{NHAc}$-βPPPPβDp |
| NV1061 | ImPPβPPP-γ$_{NH2}$-PPβPPPPβTa |
| NV1062 | ImPPβPPP-γ$_{NHAc}$-PPβPPPPβTa |
| NV1063 | ImPPβPPP-γ$_{NHAc}$-PPβPPPPβDp |
| NV1064 | ImPPβPPP-γ$_{NH2}$-PPβPPPPβDp |
| NV1065 | ImPPPIm-γ$_{NH2}$-βPPPPβDp |
| NV1066 | ImPPβPPImβP-γ$_{NH2}$-PPβPPPβPPPβDp |
| NV1067 | ImPPβPImβPP-γ$_{NH2}$-PPβPPPβPPPβTa |
| NV1068 | ImPPβPImβPP-γ$_{NHAc}$-PPβPPPβPPPβDp |
| NV1069 | ImPPβPPPP-γ-PPβPPPPPPTa•3TFA |
| NV1070 | ImPPβPImβPP-γ-PPβPPβPPPPTa•4TFA |
| NV1071 | TMG-PPβPPβPPIm-γ$_{NH2}$-PβPPβPPPβPPTa•5TFA |
| NV1072 | TMG-PPβPPβPPIm-γ$_{NHR}$-PβPPβPPPβPβTa•6TFA |
| NV1073 | TMG-PPβPPβPPIm-γ$_{NH2}$-PβPPβPPPβPβTa•5TFA |
| NV1074 | TMG-PPβPPβPP-γ$_{NHR}$-PPPβPPPβPβTa•5TFA |
| NV1075 | TMG-PPβPPβPPIm-γ$_{NH2}$-PβPPβPPPβPβDp•4TFA |
| NV1076 | TMG-PPβPPβPP-γ$_{NH2}$-PPPβPPPβPβTa |
| NV1077 | TMG-PPβPPβP-γ$_{NH2}$-PPPβPPPβPβDp |
| NV1078 | TMG-PβPPImβPP-γ-PPβPPPβPPPβTa•4TFA |
| NV1079 | TMG-PPPβPPβP-γ$_{NHR}$-PPPβPPPβPβDp•3TFA |
| NV1080 | TMG-PβPPImβPP-γ-PPβPPPβPPPβDp•3TFA |
| NV1081 | TMG-PβPPP-γ-PPβPPPPβDp•2TFA |
| NV1082 | TMG-PβPPP-γ-PPβPPPPβTa•3TFA |
| NV1083 | TMG-PPβPPP-γ-PPβPPPPβDp•2TFA |
| NV1084 | TMG-PPβPPP-γ-PPβPPPPβTa•3TFA |
| NV1085 | TMG-PPβPPImβP-γ-PPβPPPβPPPβTa |
| NV1086 | TMG-PPβPPImβPP-γ-PPβPPPβPPPβDp |
| NV1087 | TMG-PPPβPPβPIm-γ-PβPPβPPPβPβTa |
| NV1088 | TMG-PPPβPPβPIm-γ-PβPPβPPPβPβDp |
| NV1089 | TMG-PpβPPβPIm-γ-PβPPβPPPβPβDp |
| NV1090 | TMG-PpβPPβPIm-γ-PβPPβPPPβPβTa |
| NV1092 | ImPPβPP-γ-PPβPPPPβTa |
| NV1093 | ImPPβPPImβP-γ-PPβPPPβPPPβTa |
| NV1094 | TMG-PImβP-γ-PPPβPPPβTa |
| NV1095 | TMG-PPβPPβP-γ$_{NH2}$-PPPβPPPβPβTa |
| NV1096 | TMG-PpβPPβPIm-γ$_{NH2}$-PβPPβPPPβPβTa |
| NV1097 | TMG-PPβPPβP-γ-PPPβPPPβPβ-Ta•3TFA |
| NV1098 | TMG-PPPβPPβP-γ-PPPβPPPβPβ-Ta•3TFA |
| NV1101 | TMG-PyPyPyβPyPyβPyIm-γ-PyβPyPyβPyPyPyβPyβ-Ta-FAM (3 TFA) |
| NV1102 | TMG-PImPIm-γ-PPPPβTa |
| NV1103 | TMG-PImβIm-γ-PβPPPβTa |
| NV1104 | TMG-PImPIm-γ-PβPPPβTa |
| NV1105 | TMG-PImβIm-γ-PPPPβTa |
| NV1106 | Guan-PImβImPβPPβTa |
| NV1107 | Guan-PPβPPImβPP-γ-PPβPPPβPPPβTa (4 TFA) |
| NV1108 | Guan-PPβPPP-γ-PPβPPPPβTa (3 TFA) |
| NV1109 | Guan-PPβPPImβPP-γ-PPβPPPβPPPβDp (3 TFA) |
| NV1110 | Guan-PPβPPP-γ-PPβPPPPβDp (2 TFA) |
| NV1111 | Guan-PPβPPβPIm-γ-PβPPβPPPβPβTa (4 TFA) |
| NV1112 | Guan-PPβPPβPIm-γ-PβPPβPPPβPβDp (3 TFA) |
| NV1113 | TMG-IPPβPPP-γ-PPβPPPPβTa (4 TFA) |
| NV1114 | TMG-IPPβPPPIβPP-γ-PPβPPPβPPPβTa (5 TFA) |
| NV1115 | Guan-IPPβPPP-γ-PPβPPPPβTa (4 TFA) |
| NV1116 | Guan-IPPβPPPIβPP-γ-PPβPPPβPPPβTa (5 TFA) |
| NV1117 | IPPβPPP-γ-PPβPPPPβTa-BODIPY-FLX (2 TFA) |
| NV1118 | Ac-IPPβPPIβPP-γ-PPβPPPβPPPβTa (5 TFA) |
| NV1119 | PPβPPβPIm-γ-PβPPβPPPβPβTa |
| CHC2001 | ImPPβPPP-γ-PPβPPPPβTa (3 HCO$_2$H) |
| CHC2002 | ImPPPβPP-γ-PPPβPPPβTa (3 HCO$_2$H) |
| KJK6045f26-28 | TMG-ImPβPPP-γ-PβPPPPβTa (4 HCO$_2$H) |
| KJK6047-1 | Guan-ImPβPPP-γ-PβPPPPβTa (4 HCO$_2$H) |
| KJK6048 | ImPβPPP-γ-PβPPPPβTa (3 HCO$_2$H) |
| KJK6049 | ImPPβPP-γ-PPβPPPPβTa (3 HCO$_2$H) |
| KJK6050f16-18 | TMG-ImPPβPP-γ-PPβPPPPβTa (4 HCO$_2$H) |
| KJK6062 | Guan-ImPPβPP-γ-PPβPPPPβTa (4 HCO$_2$H) |
| KJK6065f17-19 | TMG-PPImβPP-γ-PPβPPPβTa (4 HCO$_2$H) |
| KJK6067f12 | Guan-PPImβPP-γ-PPβPPPβTa (4 HCO$_2$H) |
| KJK6068f20-22 | PPImβPP-γ-PPβPPPβTa (3 HCO$_2$H) |
| KJK6076 | ImPPβPPImβPP-γ-PPβPPPβPPPβTa (4 HCO$_2$H) |
| KJK6099 | ImPPPβPP-γ-PPPβPPPβDp (2 TFA) |
| FT1138 | ImPPβPPImβPP-γ-PPβPPPβPPPβTa-AF488 (HCO$_2$H) |
| FT1139 | ImImPIm-γ-PβPPPβTa-AF488 (2 HCO$_2$H) |

In accordance with the foregoing:

GUAN = guanidinyl radical;

TMG = tetramethylguanidinyl;

P = 4-amino-2-carbonyl-N-methylpyrrole;

γ = gamma-aminobutyric acid;

γ$_{NH2}$ = (R)-2,4-diaminobutyric acid reacted through either the 2-amino group or the 4-amino group;

γ$_{NHAc}$ = (R)-2-(acetylamino)-4-aminobutyric acid;

β = beta-alanine;

Im = 4-amino-2-carbonyl-N-methylimidazole;

Ta = 3,3'-diamino-N-methyldipropylamine;

Dp = (dimethylamino)propylamine;

TFA = trifluoroacetic acid;

HCO$_2$H = formate;

AF488—AlexaFluor-488 fluorophore; and

α means that the γ-aminobutyric acid formed an α-linked hairpin rather than the typical γ-linked hairpin; and AF488 = AlexaFluor-488 fluorophore In an embodiment, the guanidinyl radical is unsubstituted (i.e., the nitrogen atoms in the guanidinyl radical do not bear any substituents other than hydrogen). In an embodiment, the guanidinyl radical is monosubstituted or gem-disubstituted, or is N,N'-disubstituted, N,N,N'-trisubstituted, or N,N,N',N'-tetrasubstituted. In a further embodiment, a guanidinylated polyamide in accordance with the invention may be N,N',N'-trisubstituted.

FIGS. 9A and 9B illustrate various types of guanidinyl radicals, including different substitution patterns and tautomers, which may be present in the polyamides of the present invention.

TABLE 2

Polyamide compounds used for evaluating anti-polyomavirus activity and/or anti-papillomavirus activity.

| Compound | Molecular formula of free base | calc. exact mass M | calc. avg. MW | HPLC/MW (ESI+) | HRMS |
|---|---|---|---|---|---|
| NV1071 | $C_{114}H_{145}N_{41}O_{20}$ | 2408.159 | 2409.63 | 2409.8 [M + H]+<br>1205.5 [M + 2H]$^{2+}$ | 2408.14725 [M]+ |
| NV1072 | $C_{125}H_{167}N_{45}O_{22}$ | 2650.3332 | 2651.95 | 1326.5 [M + 2H]$^{2+}$ | 2650.31905 [M]+ |
| NV1073 | $C_{117}H_{150}N_{42}O_{21}$ | 2479.1961 | 2480.71 | 2481.0 [M + H]+<br>1241.0 [M + 2H]$^{2+}$ | 2479.18193 [M]+ |
| NV1074 | $C_{117}H_{157}N_{41}O_{20}$ | 2456.2529 | 2457.76 | 2458.2 [M + H]+<br>1229.5 [M + 2H]$^{2+}$ | 2456.24158 [M]+ |
| NV1075 | $C_{115}H_{145}N_{41}O_{21}$ | 2436.1539 | 2437.64 | 2438.2 [M + H]+<br>1219.5 [M + 2H]$^{2+}$ | 2436.14773 [M]+ |
| NV1076 | $C_{109}H_{140}N_{38}O_{19}$ | 2285.1157 | 2286.52 | 2287.0 [M + H]+<br>1144.0 [M + 2H]$^{2+}$ | 2285.10297 [M]+ |
| NV1077 | $C_{107}H_{135}N_{37}O_{19}$ | 2242.0735 | 2243.45 | 2244.0 [M + H]+<br>1122.3 [M + 2H]$^{2+}$ | 2242.0638 [M]+ |
| NV1078 | $C_{114}H_{144}N_{40}O_{20}$ | 2393.1481 | 2394.62 | 2395.0 [M + H]+<br>1198.0 [M + 2H]$^{2+}$ | 2393.13581 [M]+ |
| NV1079 | $C_{113}H_{147}N_{39}O_{20}$ | 2370.1685 | 2371.63 | 2372.0 [M + H]+<br>1186.5 [M + 2H]$^{2+}$ | 2370.15878 [M]+ |
| NV1080 | $C_{112}H_{139}N_{39}O_{20}$ | 2350.1059 | 2351.55 | 2352.0 [M + H]+<br>1176.5 [M + 2H]$^{2+}$ | 2350.09462 [M]+ |
| NV1081 | $C_{83}H_{106}N_{28}O_{14}$ | 1718.8443 | 1719.91 | 1720.5 [M + H]+<br>860.5 [M + 2H]$^{2+}$ | 1718.834 [M]+ |
| NV1082 | $C_{85}H_{111}N_{29}O_{14}$ | 1761.8865 | 1762.98 | 1763.5 [M + H]+<br>882.0 [M + 2H]$^{2+}$ | 1761.8757 [M]+ |
| NV1083 | $C_{89}H_{112}N_{30}O_{15}$ | 1840.8923 | 1842.03 | 1842.5 [M + H]+<br>921.5 [M + 2H]$^{2+}$ | 1840.88244 [M]+ |
| NV1084 | $C_{91}H_{117}N_{31}O_{15}$ | 1883.9345 | 1885.1 | 1885.5 [M + H]+<br>943.0 [M + 2H]$^{2+}$ | 1883.92375 [M]+ |
| NV1085 | $C_{120}H_{150}N_{42}O_{21}$ | 2515.1961 | 2516.74 | 2517.0 [M + H]+<br>1259.0 [M + 2H]$^{2+}$ | 2515.18393 [M]+ |
| NV1086 | $C_{118}H_{145}N_{41}O_{21}$ | 2472.1539 | 2473.68 | 2474.0 [M + H]+<br>1237.5 [M + 2H]$^{2+}$ | 2472.14515 [M]+ |
| NV1087 | $C_{117}H_{149}N_{41}O_{21}$ | 2464.1852 | 2465.7 | 2466.0 [M + H]+<br>1233.5 [M + 2H]$^{2+}$ | 2464.1686 [M]+ |
| NV1088 | $C_{115}H_{144}N_{40}O_{21}$ | 2421.143 | 2422.63 | 2423.0 [M + H]+<br>1212.0 [M + 2H]$^{2+}$ | 2421.12661 [M]+ |
| NV1089 | $C_{109}H_{138}N_{38}O_{20}$ | 2299.095 | 2300.5 | 2300.8 [M + H]+<br>1151.0 [M + 2H]$^{2+}$ | 2299.116 [M]+ |
| NV1090 | $C_{111}H_{143}N_{39}O_{20}$ | 2342.1372 | 2343.57 | 2343.8 [M + H]+<br>1172.5 [M + 2H]$^{2+}$ | 2342.15 [M]+ |
| NV1094 | $C_{84}H_{110}N_{30}O_{14}$ | 1762.8818 | 1763.96 | 1763.8 [M + H]+<br>882.5 [M + 2H]$^{2+}$ | 1762.8907 [M]+ |
| NV1095 | $C_{103}H_{134}N_{36}O_{18}$ | 2163.0677 | 2164.4 | 1083.0 [M + 2H]$^{2+}$ | |
| NV1096 | $C_{111}H_{144}N_{40}O_{20}$ | 2357.1481 | 2358.59 | 1180.0 [M + 2H]$^{2+}$ | 2358.17183 [M + H]+ |
| NV1097 | $C_{103}H_{133}N_{35}O_{18}$ | 2148.0574 | 2149.39 | 2149.8 [M + H]+<br>1075.5 [M + 2H]$^{2+}$ | 2148.051 [M]+ |
| NV1098 | $C_{109}H_{139}N_{37}O_{19}$ | 2270.1054 | 2271.51 | 2271.8 [M + H]+<br>1136.5 [M + 2H]$^{2+}$ | |
| NV1101 | $C_{138}H_{160}N_{41}O_{27}$ | 2823.2407 | 2825.01 | 1412.5 [M + 2H]$^{2+}$ | |
| NV1102 | $C_{65}H_{87}N_{25}O_{10}$ | 1377.70716 | 1378.56 | 1378.6 [M + H]+<br>689.8 [M + 2H]$^{2+}$ | 1377.7012 |
| NV1103 | $C_{59}H_{85}N_{23}O_{10}$ | 1275.6801 | 1276.46 | 1276.6 [M + H]+<br>638.8 [M + 2H]$^{2+}$ | 1275.6801 |
| NV1104 | $C_{62}H_{86}N_{24}O_{10}$ | 1326.69626 | 1327.51 | 1327.6 [M + H]+<br>664.4 [M + 2H]$^{2+}$ | 1326.6897 |
| NV1105 | $C_{62}H_{86}N_{24}O_{10}$ | 1326.69626 | 1327.51 | 1327.6 [M + H]+<br>664.4 [M + 2H]$^{2+}$ | 1326.69 |
| NV1106 | $C_{55}H_{77}N_{23}O_{10}$ | 1219.6227 | 1220.35 | 1220.4 [M + H]+<br>610.8 [M + 2H]$^{2+}$ | 2408.14725 [M]+ |

TABLE 3

Polyamide sequences and HRMS for compounds used for evaluating anti-polyomavirus activity.

| Polyamide # | Polyamide Sequence | Theor. MS | Actual MS |
|---|---|---|---|
| NV1002 | ImPPβPP-γ-PPβPPPβDp | 1850.8403 | 1850.8408 |
| NV1021 | ImImPIm-γ-pImPPβDp | 1223.5597 | 1223.5611 |
| NV1028 | ImPPβPPP-γ-PPβPPPPβTa | MH+ = 1894.8908 | 1894.8933 |
| NV1029 | ImPPβPPβ-γ$_{NH2}$-PPβPPPPβPβDp | 2007.9254 | 2007.9282 |
| NV1030 | ImPPβPPP-γ$_{NH2}$-PPβPPPPβTa | MH+ = 1909.9018 | 1910.9064 |
| NV1039 | OHC-PPPPPPβDp | 933.4358 | 933.4371 |
| NV1042 | ImPPβPPImβPP-γ-PPβPPPβPPPβTa | MH+ = 2526.1447 | 2526.1557 |
| NV1054 | Ac-βPPP-γ-PPβPPPPβTa | MH+ = 1583.7647 | 1583.7709 |
| NV1055 | Ac-PβPPP-γ-PPβPPPPβTa | MH+ = 1705.8127 | 1705.8182 |
| NV1056 | ImPPPβPPβ-γ-PPβPPPβPPDp | 2043.9254 | 2043.9283 |
| NV1058 | ImPPPIm-γ$_{NH2}$-βPPPPβTa | MH+ = 1473.7157 | 1473.7155 |
| NV1059 | ImPPPIm-γ$_{NHAc}$-βPPPPβTa | MH+ = 1515.7263 | 1515.7280 |
| NV1060 | ImPPPIm-γ$_{NHAc}$-βPPPPβDp | MH+ = 1472.6841 | 1472.6855 |
| NV1065 | ImPPPIm-γ$_{NH2}$-βPPPPβDp | MH+ = 1430.6735 | 1430.6738 |
| NV1066 | ImPPβPPImβPP-γ$_{NH2}$-PPβPPPβPPPβDp | MH+ = 2497.1128 | 2497.1335 |
| NV1067 | ImPPβPPImβPP-γ$_{NH2}$-PPβPPPβPPPβTa | 2540.1550 | 2540.1783 |
| NV1068 | ImPPβPPImβPP-γ$_{NHAc}$-PPβPPPβPPPβDp | 2539.1233 | 2539.1348 |
| NV1070 | ImPPβPPImβPP-γ-PPβPPPβPPPPTa | MH+ = 2577.1628 | 2577.1153 |
| NV1071 | TMG-PPβPPβPIm-γ$_{NH2}$-PβPPPβPPPβPPTa | 2408.1590 | 2408.1472 |
| NV1072 | TMG-PPPβPPβPIm-γ$_{NHR}$-PβPPPβPPPβPβTa | 2650.3332 | 2650.3190 |
| NV1073 | TMG-PPPβPPβPIm-γ$_{NH2}$-PβPPPβPPPβPβTa | 2479.1961 | 2479.1819 |
| NV1078 | TMG-PβPPImβPP-γ-PPβPPPβPPPβTa | 2393.1481 | 2393.1358 |
| NV1079 | TMG-PPPβPPβPbP-γ$_{NHR}$-PPPβPPPPβPβDp | 2370.1685 | 2370.1588 |
| NV1080 | TMG-PβPPImβPP-γ-PPβPPPβPPPβDp | 2350.1059 | 2350.0946 |
| NV1081 | TMG-PβPPP-γ-PPβPPPPβDp | 1718.8443 | 1718.8340 |
| NV1082 | TMG-PβPPP-γ-PPβPPPPβTa | 1761.8865 | 1761.8757 |
| NV1083 | TMG-PPβPPP-γ-PPβPPPPβDp | 1840.8923 | 1840.8824 |
| NV1084 | TMG-PPβPPP-γ-PPβPPPPβTa | 1883.9345 | 1883.9238 |
| NV1085 | TMG-PPβPPImβPP-γ-PPβPPPβPPPβTa | 2515.1961 | 2515.1839 |
| NV1086 | TMG-PPβPPImβPP-γ-PPβPPPβPPPβDp | 2472.1539 | 2472.1452 |
| NV1087 | TMG-PPPβPPβPIm-γ-PβPPPβPPPβPβTa | 2464.1852 | 2464.1686 |
| NV1088 | TMG-PPPβPPβPIm-γ-PβPPPβPPPβPβDp | 2421.1430 | 2421.1266 |
| NV1089 | TMG-PPβPPβPIm-γ-PβPPβPPPPβPβDp | 2299.0950 | 2299.1160 |
| NV1090 | TMG-PPβPPβPIm-γ-PβPPβPPPPβPβTA | 2342.1372 | 2342.1500 |
| NV1092 | ImPPβPP-γ-PPβPPPPβTa | 1771.83498 | 1771.8333 |
| NV1093 | ImPPβPPImβP-γ-PPβPPPβPPPβTa | 2403.0967 | 2403.0924 |
| NV1097 | TMG-PPβPPβP-γ-PPPβPPPPβPβTa | 2148.0574 | 2148.0510 |
| NV1098 | TMG-PPPβPPβP-γ-PPPβPPPPβPβ-Ta | 2270.1048 | 2270.1099 |

TABLE 3-continued

Polyamide sequences and HRMS for compounds used for evaluating anti-polyomavirus activity.

| Polyamide # | Polyamide Sequence | Theor. MS | Actual MS |
|---|---|---|---|
| NV1104 | TMG-PImPIm-γ-PβPPβTa | 1326.6963 | 1326.6897 |
| NV1106 | Guan-PImβIm-γ-PβPPβTa | 1219.6223 | 1219.6190 |
| NV1107 | Guan-PPβPPImβPP-γ-PPβPPPβPPPβTa | 2459.1334 | 2459.1157 |
| NV1108 | Guan-PPβPPP-γ-PPβPPPPβTa | 1827.8719 | 1827.8608 |
| NV1109 | Guan-PPβPPImβPP-γ-PPβPPPβPPPβDp | 2416.0912 | 2416.0769 |
| NV1110 | Guan-PPβPPP-γ-PPβPPPPβDp | 1784.8297 | 1784.8185 |
| NV1111 | Guan-PPPβPPβPIm-γ-PβPPβPPPβPβTa | 2408.1225 | 2408.1075 |
| NV1112 | Guan-PPPβPPβPIm-γ-PβPPβPPPβPβDp | 2365.0803 | 2365.0657 |
| NV1113 | TMG-IPPβPPP-γ-PPβPPPPβTa | 2006.9778 | 2006.9653 |
| NV1114 | TMG-IPPβPPIβPP-γ-PPβPPPβPPPβTa | 2638.2393 | 2638.2232 |
| NV1115 | Guan-IPPβPPP-γ-PPβPPPPβTa | 1950.9152 | 1950.9034 |
| NV1116 | Guan-IPPβPPIβPP-γ-PPβPPPβPPPβTa | 2582.1767 | 2582.1607 |

MS values listed represent M+ unless noted otherwise.
TMG- = tetramethylguanidinyl, Guan- = guanidinyl, Ac = N-acetyl, OHC = N-formyl, R = CO (CH2)3 N(CH3) (CH2)3 NH2, R' = CO (CH2)3 N(CH3)2; other building blocks are defined above.

Polyamide-DNA binding has been reported to interfere with protein-DNA binding, and polyamides have been reported to inhibit gene expression, presumably through competition with transcription factors for DNA binding sites.

The present invention provides methods for treating polyomavirus and/or papillomavirus infections and other diseases by administering polyamides and analogs of polyamide polymers.

Figure 6:
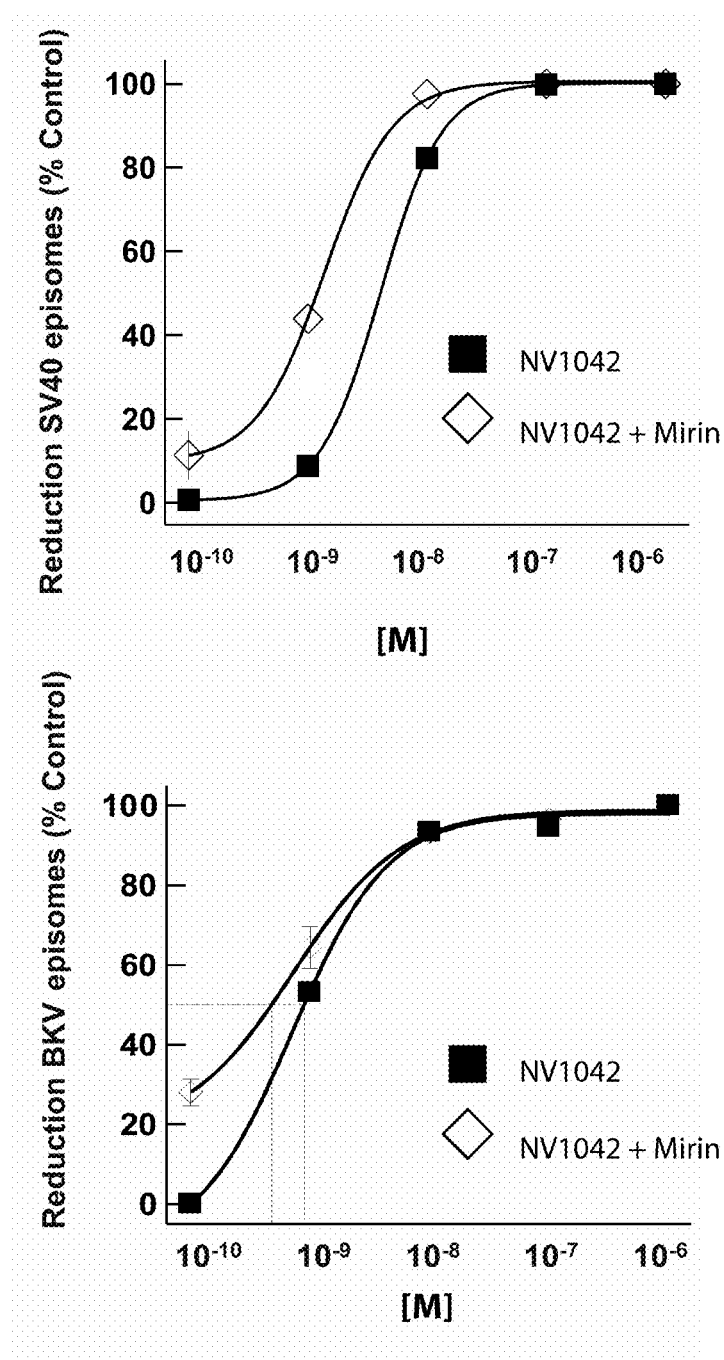
FIG. 6: Pharmacologic inhibition of MRE11 sensitizes SV40 and BKV episomes to NV1042. The IC$_{50}$ for NV1042 against SV40 and BKV is 32 nM and 9 nM respectively without Mirin (solid boxes), and 12 nM and 5 nM in the presence of 100 μM Mirin (open diamonds). Treatment with 1000 Mirin alone had no effect on episome levels. n=3 independent experiments, error bars represent the standard error of the mean. We reported the same effect for HPV: inhibition of MRE11 sensitizes HPV episomes to elimination by MV1042 (PA25). (Edwards T G, Vidmar T J, Koeller K, Bashkin J K, Fisher C (2013) DNA Damage Repair Genes Controlling Human Papillomavirus (HPV) Episome Levels under Conditions of Stability and Extreme Instability. PLoS ONE 8(10): e75406. doi:10.1371/journal.pone.0075406).
Figure 7:
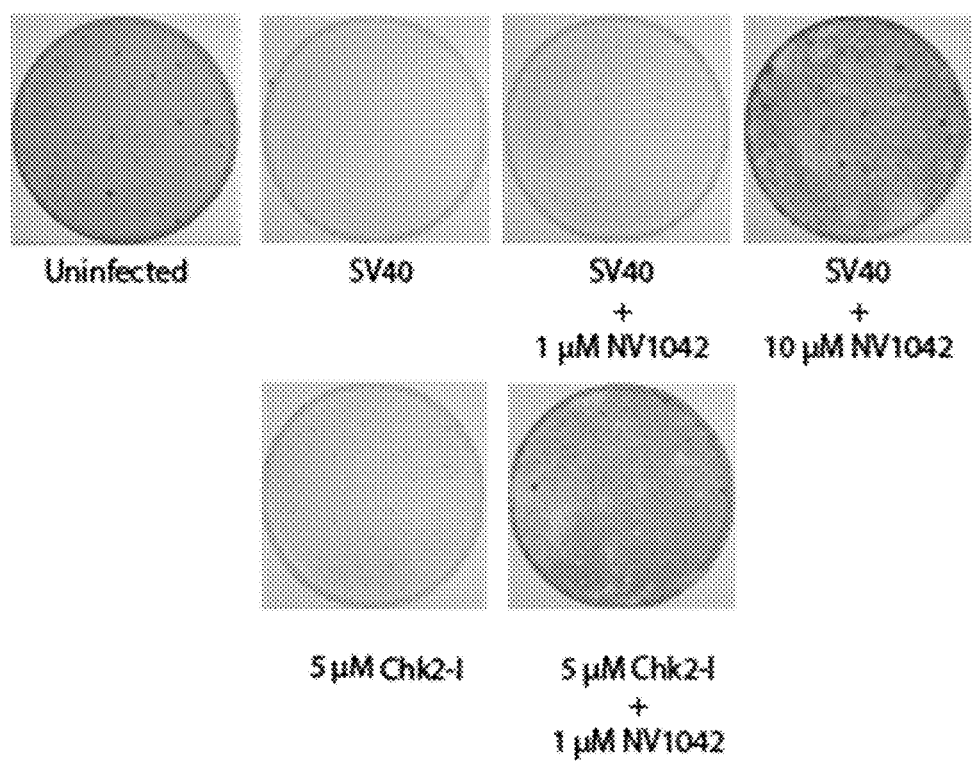
FIG. 7: Activity of polyamide and cell survival is promoted by inhibition of the Chk2 kinase which acts downstream of the ATM kinase during a DDR. As in the case of Mirin (FIG. 6), the sensitivity of viral DNA towards treatment with polyamide is enhanced by pretreatment with the Chk2-I (Sigma). 1 μM NV1042 is not effective at preventing the cytopathic effect (CPE) and cell loss following 2 weeks of infection but inhibition of Chk2 kinase with Chk2 inhibitor dramatically enhances polyamide antiviral and cell protective ability.
Figure 8:
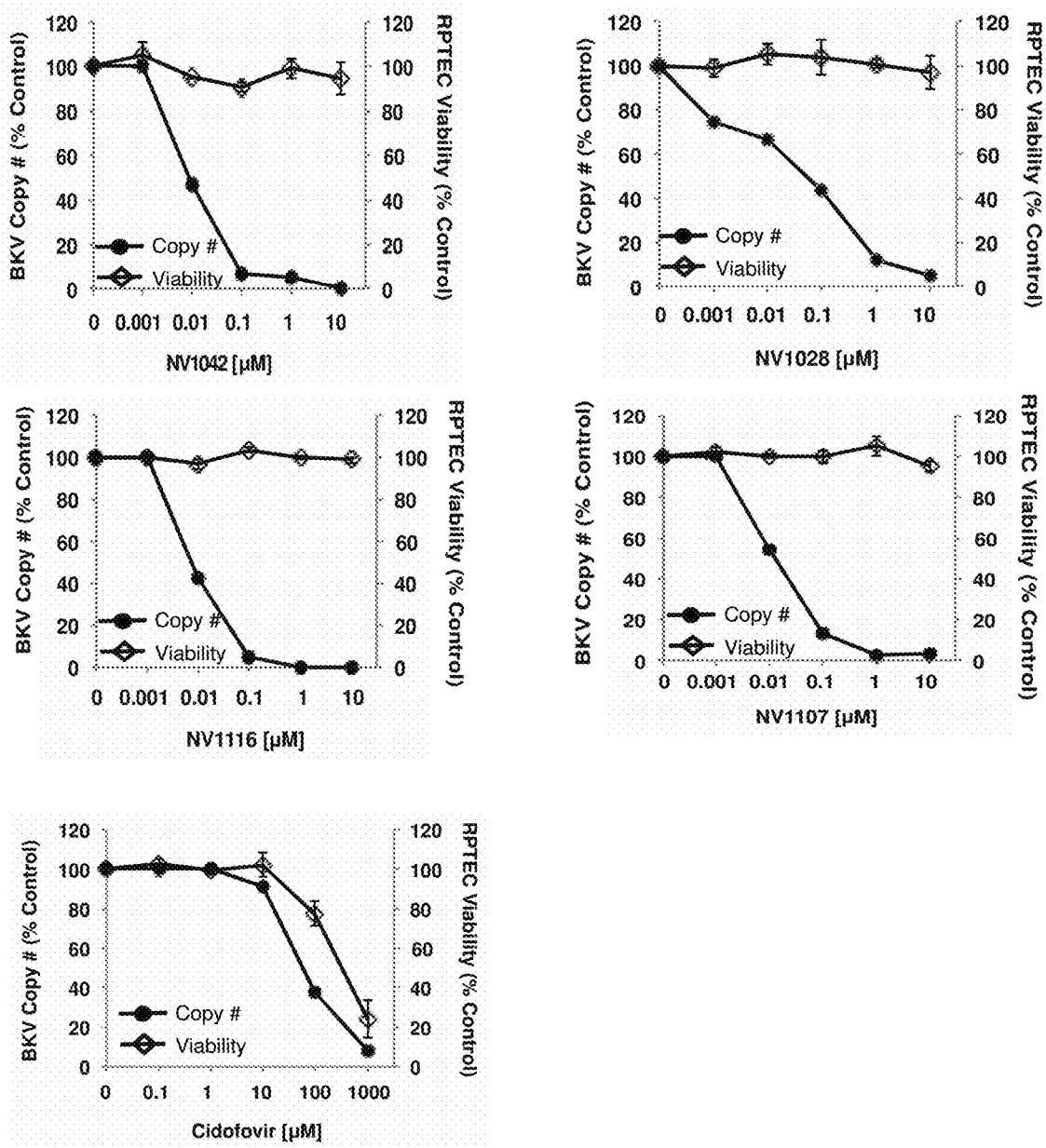
FIG. 8: Loss of viral BKV copies in response to 4 different polyamides compared with toxicity of the same polyamides in RPTECs. No toxicity is exhibited by the 4 polyamides at the highest dose of 10 μM, while their $IC_{50}$ values are in the low nanomolar range. Cidofovir, on the other hand, an antiviral that has been used for treatment of PyVAN patients, exhibits toxicity and low potency against BKV.

Time-course experiments of the anti-PyV action of the polyamides of this invention lead to the discovery that a single dose of certain active molecules delivered to polyomavirus-infected renal proximal tubule epithelial cells (RPTECs) on day 2 post-infection, causes a significant reduction in viral copy numbers as late as 11 days post-infection, as shown in FIG. 6.

PyV establishes it's small, circular, chromatinized, super-coiled genomes in the nucleus of infected cells. Without being bound by theory, polyamides used in the present invention can bind the circular PyV and/or HPV genomes, causing changes within the viral episomes that are recognized and not tolerated by the host cells. Cellular mechanisms are then activated, resulting in the rapid loss and degradation of the episome. Thus, binding of polyamides to DNA activates a process resulting in specific elimination of viral rather than host DNA sequences.

The polyamides described herein provide a therapeutic agent to target PyV and/or HPV. Possible targets within the viruses may include sequences required for tethering, maintenance, or replication, or the polyamides may trigger cellular recognition of the viral DNA as foreign resulting in its clearance.

In still yet other embodiments, the polyamides used in combination with other antivirals, such as, without limitation, Interferon, cidofovir, CMX-001, leflunomide, adefovir, entecavir, lamivudine, telbivudine, or tenofovir, acyclovir and other Herpes/cytomegaloviral drugs, and anti-HIV drugs. The polyamides can also be used in combination with photodynamic therapy, radiation therapy and chemotherapy.

Administration of a "therapeutically effective amount" of a pharmaceutical composition comprising the polyamides of the invention results in treating or lessening the severity of PyV and papillomavirus infections in subjects infected with PyV or HPV. The therapeutically effective amount of a pharmaceutical composition comprises the active polyamides in a unit dosage form which is amenable to administration to a subject for the efficacious treatment of a viral infection. Such pharmaceutical compositions and unit dosage forms may facilitate patient compliancy and may comprise conventional or new ingredients in conventional or special proportions, with or without additional active compounds or principles, and such unit dosage forms may contain any suitable effective amount of the active ingredient commensurate with the intended dosage range to be employed for facile and efficacious treatment of viral infections.

The active pharmaceutical ingredients of the invention, together with one or more conventional adjuvants, carriers, or diluents, may be placed into the form of pharmaceutical compositions and unit dosages thereof, and in such form may be employed as solids (e.g., coated or uncoated tablets or filled capsules), or liquids or semi-solids (e.g., solutions, suspensions, emulsions, gels, elixirs, or capsules filled with the same), for oral or mucosal use as well as injectables.

The term "carrier" applied to pharmaceutical compositions of the invention refers to a diluent, excipient, or vehicle with which an active compound is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil, Dimethysulfoxide (DMSO) or D5W vehicle, and the like. Suitable pharmaceutical carriers are described in "Remington's Pharmaceutical Sciences" by E. W. Martin, 18$^{th}$ Edition.

Polyamides can be in the form of pharmaceutically acceptable salts such as trifluoroacetate (TFA) salts, formate salts, as well as chloride, succinate, ascorbate salts and the like. They can also be formulated with excipients such as PEG-400, propylene glycol and the like.

To increase stability, the polyamide drug may be placed in aqueous solution with an antioxidant such as ascorbic acid, BHT or BHA in order to develop a more stable formula. (See Mayers C. L., et al. (1993) Pharma Res, 10: 445-448, and Stuhar M., (1984) Farmaceuticky Obzor, 53; 499-504).

For delivery to the vagina and cervix, polyamides may be formulated as solutions, emulsions, suspensions, tablets, gels, foams, suppositories, films, sponges and vaginal rings. Formulations include gels (e.g., gels prepared using gelling agents such as hydroxy ethyl cellulose and polyacrylic acids, e.g., cross-linked acrylic acid based polymers such as those sold under the brand name CARBOPOL®), and polyvinyl alcohol films that can be administered by an applicator to the target site. Alternatively, lower viscosity liquid formulations (e.g. Polyethylene glycol solutions) can be delivered in a polyurethane sponge to the area around the cervix. (Okada, (1991) in "Peptide and Protein Drug Delivery" V. H. Lee, ed., pp. 663-666, Marcel Dekker, NY; Garg, et al. (2001) Pharm. Tech. 25:14-24). Because of the polyamides' charge, the polyamides may be formulated in a controlled delivery vehicle by using carbomers (such as those sold under the brand name CARBOPOL®). If the polyamide has a charge of +1 or +2, by adjusting the ionic strength of the formulation one may bind the polyamide electrostatically to the carbomer and thereby control the release rate. In a semisolid dosage form, the release rate may be evaluated in a membrane apparatus as described in the US Pharmacopeia (Dipiano, et al., PCT International Publication No. WO 04/064913) for drug diffusion from semisolid dosage forms. Polyamides formulated in carbomer-based gels which exhibit significant yield stresses, and also have potential bioadhesive properties (Kieweg, et al. (2004) J. Pharm Sci. 93, 2941-52.

Any of the excipients used for commercial vaginal formulations (Garg et al., 2001) may be adapted for use with the polyamide compounds of the present invention. A number of commonly used excipients such as PEG (polyethylene glycol), PVA (polyvinyl alcohol) and Tween surfactants can also be employed. In addition to antioxidants, further compatibilizers or stabilizers may be used. Solid forms may allow for more stable formulas with a longer shelf life due to their physical state. Emulsions made from bioadhesives using polymers such as carbomers may be useful. HPMC (hydroxymethylpropyl cellulose), PVA and lipid complexes can be used with lower solubility drugs. Lipidic systems may then be suspended in a viscoelastic gel for delivery of the insoluble polyamide.

For more sustained or effective delivery, cervical barrier devices available such as diaphragms that can deliver the drug at the cervix site over many hours can be used for delivery that is even more continuous vaginal rings or slow release implantable polymer films can be employed. In addition, several new vaginal delivery systems in clinical testing such as vaginal sponge technology and the SILOS diaphragm, a single size silicone device that can deliver drug to both the cervix and vaginal wall (Cohen, (2004) The Microbiocide Quarterly, 2:15-19) may be used. For improved continuous delivery of the drug over an extended period, vaginal rings are available with slow release of the drug from the ring composite (Cohen, 2004; Hussain and Ahsan, (2005), J. Controlled Release 103:301-13). There are also numerous other applicators and formulas that have been developed for controlled vaginal drug delivery (Robinson (1999) Proc. Of the 26th Intl. Symp. Controlled Release of Bioactive Materials, 26:2-3; Hussain and Ahsan, 2005).

Formulations for transdermal delivery include lipid-based formulas for delivery of protein pharmaceuticals to genital warts (Foldvari et al., (1999), Biotech. Appl. Biochem. 30:129-37; Leigh (2003) Drugs and the Pharm. Sci., 126: 791-800; Lee et al., (2004) Biomaterials, 26:205-10), bioadhesives formulations (Bogataj and Mrhar (1998) Bioadhesive mucosal drug delivery systems, 49:445-57; Amaral et al. (1999) Contraception, 60:361-66; Barry, (1987) in "Drug Delivery systems", Johnson and Lloyd-Jones, eds, Ch. 11, Ellis Horwood, Chichester; Vermani, et al. (2002) Drug Dev. Indust. Pharm. 28:1133-46) and novel polymer systems. The novel polymers include partially absorbable biodegradable antiviral intravaginal rings (Shalaby, (2005) U.S. Patent Application Publication No. 2005/053639), bilaminar bioadhesive polymeric films applied directly to the cervix (Sidhu et al., (1997) Br. J. Obstetrics and Gynaecology, 104:145-49) novel, slow-release polymer discs at the cervical mucosa and thermogelling systems that have the advantage of potentially much greater bioadhesion and dosage form retention. (Saltzman and Radomsky (1990) Polymer Preprints, 31:245-46; Edelman and Mark (1998) Nature Biotech, 16:136-37). Polyamides may also be formulated using cell membrane penetrating peptides (Gupta, et al. (2005) Adv. Drug Del Rev. 57:637-51; Wadia and Dowdy (2005) Adv. Drug Del. Rev., 57:579-96.

The polyamides of the present invention can also be formulated with a pharmaceutically-acceptable polymer designed to shorten or lengthen time before renal clearance.

Polyamides in accordance with the present invention can also be formulated to deliver an aerosol treatment of the lungs, mouth or throat. Direct injection into HPV lesions may also be employed for external (cutaneous) or mucosal skin infections.

Other disease indications may require systemic treatment with the present polyamides, i.e., by injection, or additional, common or known drug delivery methods.

It will also be appreciated that certain compounds of the present invention can exist in free form for treatment, or where appropriate, as a pharmaceutically acceptable derivative or a prodrug thereof. According to the present invention, a pharmaceutically acceptable derivative or a prodrug includes, but is not limited to, pharmaceutically acceptable salts, esters, salts of such esters, or any other adduct or derivative which upon administration to a subject in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof.

Pharmaceutically acceptable salts are well known in the art. For example, S. M. Berge, et al. describes pharmaceutically acceptable salts in detail in J. Pharmaceutical Sciences, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, including trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention comprise, in addition to one or more polyamide compounds, a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

In an embodiment, the present invention provides polyamides and analogs of polyamides which are useful for treating polyomavirus infections. Table 4 presents a summary of measured $IC_{50}$ values and $IC_{50}$ values of certain polyamides against polyomaviruses.

TABLE 4

Activity of polyamides against SV40 and BKV

| Polyamide # | SV40 ($IC_{50}$) | SV40 ($IC_{90}$) | BKV-Dun ($IC_{50}$) | BKV-Dun ($IC_{90}$) | BKV-TU ($IC_{50}$) | BKV-TU ($IC_{90}$) |
|---|---|---|---|---|---|---|
| NV1111 | 0.005 | 0.031 | 0.003 | 0.045 | 0.026 | 0.101 |
| NV1071 | 0.006 | 0.156 | 0.003 | 0.049 | 0.006 | 0.017 |
| NV1112 | 0.012 | 0.072 | 0.002 | 0.016 | 0.003 | 0.028 |
| NV1078 | 0.017 | 0.308 | 0.012 | 0.084 | 0.016 | 0.093 |
| NV1072 | 0.024 | 0.123 | 0.008 | 0.057 | 0.006 | 0.061 |
| NV1042 | 0.032 | 0.161 | 0.009 | 0.063 | 0.010 | 0.057 |
| NV1085 | 0.033 | 0.375 | 0.004 | 0.062 | 0.002 | 0.015 |
| NV1088 | 0.034 | 0.097 | 0.002 | 0.023 | 0.002 | 0.014 |
| NV1087 | 0.035 | 0.099 | 0.006 | 0.078 | 0.003 | 0.038 |
| NV1107 | 0.036 | 0.557 | 0.002 | 0.013 | 0.012 | 0.147 |
| NV1098 | 0.037 | 0.154 | 0.004 | 0.134 | 0.003 | 0.057 |
| NV1070 | 0.040 | 0.136 | 0.055 | 0.323 | 0.068 | 0.214 |
| NV1073 | 0.040 | 1.186 | 0.554 | >10 | 0.117 | 1.129 |
| NV1097 | 0.041 | 0.210 | 0.053 | 0.206 | 0.008 | 0.065 |
| NV1116 | 0.044 | 0.165 | 0.001 | 0.066 | 0.008 | 0.052 |
| NV1114 | 0.045 | 0.171 | 0.002 | 0.019 | 0.036 | 0.411 |
| NV1066 | 0.045 | 0.173 | 0.020 | 0.189 | 0.014 | 0.167 |
| NV1086 | 0.058 | 0.381 | 0.023 | 0.243 | 0.003 | 0.065 |
| NV1079 | 0.062 | 0.325 | 0.014 | 0.173 | 0.011 | 0.080 |
| NV1093 | 0.078 | 0.484 | 0.038 | 1.480 | 0.010 | 0.094 |
| NV1067 | 0.093 | 0.176 | 0.555 | 3.057 | 0.019 | 0.186 |
| NV1080 | 0.109 | 0.429 | 0.080 | 1.937 | 0.016 | 0.190 |
| NV1109 | 0.117 | 0.468 | 0.004 | 0.078 | 0.053 | 0.832 |
| NV1115 | 0.160 | 0.371 | 0.039 | 0.136 | 0.188 | 1.447 |
| NV1028 | 0.218 | 0.735 | 0.437 | 10.000 | 0.062 | 1.517 |
| NV1113 | 0.347 | 0.876 | 0.017 | 0.134 | 0.026 | 3.397 |
| NV1092 | 0.415 | 0.781 | 1.021 | >10 | 0.115 | >10 |
| NV1030 | 0.422 | 1.084 | 4.064 | >10 | 0.167 | 0.962 |
| NV1068 | 0.424 | 4.396 | 0.533 | >10 | 0.041 | >10 |
| NV1108 | 0.451 | 1.284 | 0.060 | 1.035 | 0.148 | 1.174 |
| NV1056 | 0.637 | >10 | 0.514 | 10.000 | 1.635 | >10 |
| NV1084 | 1.000 | >10 | NA | NA | 0.192 | 5.548 |
| NV1110 | 1.746 | 9.400 | 0.103 | 1.659 | 0.119 | >10 |
| NV1082 | 2.372 | 7.349 | NA | NA | 3.394 | 9.728 |
| NV1083 | 5.173 | 9.174 | NA | NA | 0.325 | >10 |
| NV1029 | 7.165 | >11 | NA | NA | NA | NA |
| NV1081 | 8.589 | >10 | NA | NA | NA | NA |

TABLE 4-continued

Activity of polyamides against SV40 and BKV

| Polyamide # | SV40 ($IC_{50}$) | SV40 ($IC_{90}$) | BKV-Dun ($IC_{50}$) | BKV-Dun ($IC_{90}$) | BKV-TU ($IC_{50}$) | BKV-TU ($IC_{90}$) |
|---|---|---|---|---|---|---|
| NV1054 | NA | NA | NA | NA | 9.309 | >10 |
| NV1055 | NA | NA | NA | NA | 1.282 | >10 |
| NV1058 | NA | NA | NA | NA | NA | NA |
| NV1059 | NA | NA | NA | NA | NA | NA |
| NV1060 | NA | NA | NA | NA | NA | NA |
| NV1065 | NA | NA | NA | NA | NA | NA |
| NV1021 | NA | NA | NA | NA | NA | NA |
| NV1039 | NA | NA | NA | NA | NA | NA |
| NV1104 | NA | NA | NA | NA | NA | NA |
| NV1106 | NA | NA | NA | NA | NA | NA |
| NV1002 | NA | NA | NA | NA | 5.668 | >10 |
| NV1089 | not tested | not tested | 0.007 | 0.266 | 0.003 | 0.051 |
| NV1090 | not tested | not tested | 0.003 | 0.053 | 0.002 | 0.016 |

In Table 4, "NA" indicates no measurable antiviral response was obtained relative to control at the highest dose tested (10 μM).
The $IC_{50}$ is the concentration of compound required for 50% decrease of viral DNA concentration in vitro.
The $IC_{90}$ is the concentration of compound required for 90% decrease in viral DNA concentration in vitro.

As shown in the figures, a single polyamide treatment caused a profound decrease of viral DNA levels for the period of infection relative to the untreated cells so that by day 12 (11 days after polyamide treatment) only 25% of the viral DNA levels found in the untreated samples was present in the treated samples.

One skilled in the art may conclude that the polyamides of the invention would provide therapeutic efficacy in clinically relevant polyomaviruses.

In an embodiment, the present invention provides polyamides and analogs of polyamides that are useful for treating HPV infections and other diseases.

Time-course experiments of the anti-HPV action of the polyamides of this invention led to the discovery that certain active molecules decrease HPV DNA levels in human keratinocytes by >90% beginning at times as short as 30 min after drug treatment.

Table 5 presents a summary of measured $IC_{50}$ values and $IC_{90}$ values of certain polyamides against HPV16, HPV18 and HPV31. The polyamides were tested in cells that maintain HPV16, HPV18 or HPV31 DNA. Cells maintaining the selected HPV were cultured for 72 hours in the presence of the polyamide. Viral DNA was then quantified using real-time PCR and compared to vehicle (DMSO)-treated control cultures. The results obtained demonstrate that the tested polyamides generally exhibited effectiveness in inhibiting replication of HPV16, HPV18 and HPV31.

TABLE 5

Activity of polyamides against HPV

| NanoVir # | HPV16 IC50 [μM] | HPV16 IC90 [μM] | HPV18 IC50 [μM] | HPV18 IC90 [μM] | HPV31 IC50 [μM] | HPV31 IC90 [μM] |
|---|---|---|---|---|---|---|
| NV1002 | NOT ACTIVE | NOT ACTIVE | NOT ACTIVE | NOT ACTIVE | NOT ACTIVE | NOT ACTIVE |
| NV1002* | 0.554 (±0.002) | 2.347 | NOT TESTED | NOT TESTED | NOT TESTED | NOT TESTED |
| NV1002* | 0.343 (±0.027) | 3.076 | NOT TESTED | NOT TESTED | NOT TESTED | NOT TESTED |
| NV1003 | 0.235 | 0.813 | 0.723 | 6.821 | 0.340 | 1.125 |
| NV1004 | 0.152 | 0.674 | 0.070 | 0.997 | 0.556 | 0.929 |
| NV1005 | NOT ACTIVE | NOT ACTIVE | NOT ACTIVE | NOT ACTIVE | NOT ACTIVE | NOT ACTIVE |
| NV1006 | NOT ACTIVE | NOT ACTIVE | NOT ACTIVE | NOT ACTIVE | NOT ACTIVE | NOT ACTIVE |
| NV1007*** | NOT ACTIVE | NOT ACTIVE | NOT ACTIVE | NOT ACTIVE | NOT ACTIVE | NOT ACTIVE |
| NV1008*** | NOT ACTIVE | NOT ACTIVE | NOT TESTED | NOT TESTED | NOT ACTIVE | NOT ACTIVE |
| NV1009*** | NOT TESTED | NOT TESTED | NOT TESTED | NOT TESTED | NOT TESTED | NOT TESTED |
| NV1010 | NOT ACTIVE | NOT ACTIVE | NOT ACTIVE | NOT ACTIVE | NOT ACTIVE | NOT ACTIVE |
| NV1011 | NOT ACTIVE | NOT ACTIVE | NOT ACTIVE | NOT ACTIVE | NOT ACTIVE | NOT ACTIVE |
| NV1012 | NOT ACTIVE | NOT ACTIVE | NOT ACTIVE | NOT ACTIVE | NOT ACTIVE | NOT ACTIVE |
| NV1013 | NOT ACTIVE | NOT ACTIVE | NOT TESTED | NOT TESTED | NOT ACTIVE | NOT ACTIVE |
| NV1014 | NOT ACTIVE | NOT ACTIVE | NOT TESTED | NOT TESTED | NOT ACTIVE | NOT ACTIVE |
| NV1015 | NOT ACTIVE | NOT ACTIVE | NOT TESTED | NOT TESTED | NOT ACTIVE | NOT ACTIVE |

TABLE 5-continued

Activity of polyamides against HPV

| NanoVir # | HPV16 IC50 [μM] | HPV16 IC90 [μM] | HPV18 IC50 [μM] | HPV18 IC90 [μM] | HPV31 IC50 [μM] | HPV31 IC90 [μM] |
|---|---|---|---|---|---|---|
| NV1016 | NOT ACTIVE | NOT ACTIVE | NOT TESTED | NOT TESTED | NOT ACTIVE | NOT ACTIVE |
| NV1017 | NOT ACTIVE | NOT ACTIVE | NOT TESTED | NOT TESTED | NOT ACTIVE | NOT ACTIVE |
| NV1018 | NOT ACTIVE | NOT ACTIVE | NOT TESTED | NOT TESTED | NOT ACTIVE | NOT ACTIVE |
| NV1019 | NOT ACTIVE | NOT ACTIVE | NOT TESTED | NOT TESTED | NOT ACTIVE | NOT ACTIVE |
| NV1020 | 4.984 | >10 | NOT TESTED | NOT TESTED | 0.301 | 2.626 |
| NV1021 | NOT ACTIVE | NOT ACTIVE | NOT ACTIVE | NOT ACTIVE | NOT ACTIVE | NOT ACTIVE |
| NV1022 | 5.206 | 9.332 | NOT TESTED | NOT TESTED | 2.195 | >10 |
| NV1023 | 5.002 | 8.991 | NOT TESTED | NOT TESTED | 0.858 | 3.946 |
| NV1024 | 4.933 | 9.374 | 7.058 | >10 | 0.888 | 6.435 |
| NV1025 | NOT ACTIVE | NOT ACTIVE | NOT TESTED | NOT TESTED | NOT ACTIVE | NOT ACTIVE |
| NV1026 | 1.011 | >10 | NOT ACTIVE | NOT ACTIVE | 0.705 | 6.878 |
| NV1027 | 0.219 | 0.640 | 0.398 | 2.12 | 0.165 | 0.777 |
| NV1028 | 0.100 | 1.113 | 0.717 | >10 | 0.108 | 0.986 |
| NV1029 | 0.133 | 0.917 | 2.571 | >10 | 0.261 | 8.950 |
| NV1030 | 0.131 | 1.326 | 0.415 | >10 | 0.127 | 1.865 |
| NV1031 | 0.378 | 2.012 | 0.470 | 9.191 | 0.244 | 0.983 |
| NV1032 | 0.315 | 4.057 | NOT ACTIVE | NOT ACTIVE | 0.165 | 2.169 |
| NV1033 | 2.035 | >10 | NOT ACTIVE | NOT ACTIVE | 2.990 | >10 |
| NV1037 | 0.146 | 0.773 | 0.092 | 0.871 | 0.027 | 0.200 |
| NV1038 | NOT ACTIVE | NOT ACTIVE | NOT ACTIVE | NOT ACTIVE | NOT ACTIVE | NOT ACTIVE |
| NV1039 | NOT ACTIVE | NOT ACTIVE | NOT ACTIVE | NOT ACTIVE | NOT ACTIVE | NOT ACTIVE |
| NV1040 | 0.994 | 6.730 | 0.579 | >10 | 0.340 | 6.615 |
| NV1041 | NOT ACTIVE | NOT ACTIVE | NOT ACTIVE | NOT ACTIVE | NOT ACTIVE | NOT ACTIVE |
| NV1042 | 0.036 | 0.351 | 0.056 | 1.462 | 0.030 | 0.510 |
| NV1043 | 7.039 | >10 | 0.456 | 10 | 5.223 | >10 |
| NV1044 | NOT ACTIVE | NOT ACTIVE | NOT ACTIVE | NOT ACTIVE | NOT ACTIVE | NOT ACTIVE |
| NV1045 | 1.378 | >10 | 0.300 | >10 | 1.648 | 8.926 |
| NV1046 | 0.250 | 3.050 | 0.190 | >10 | 0.119 | 5.278 |
| NV1047 | 1.549 | 8.561 | 4.277 | >10 | 3.943 | 8.91 |
| NV1048 | 0.137 | 4.226 | 0.411 | >10 | 0.061 | 0.882 |
| NV1049 | 0.659 | 7.145 | 0.258 | 3.432 | 1.242 | 7.348 |
| NV1050 | 0.600 | >10 | 0.997 | >10 | 0.820 | >10 |
| NV1051** | 3.97 | >10 | NOT ACTIVE | NOT ACTIVE | 0.879 | >10 |
| NV1052** | NOT ACTIVE | NOT ACTIVE | NOT ACTIVE | NOT ACTIVE | NOT ACTIVE | NOT ACTIVE |
| NV1053** | 2.240 | >10 | NOT ACTIVE | NOT ACTIVE | 0.468 | 1.845 |
| NV1054 | NOT ACTIVE | NOT ACTIVE | NOT ACTIVE | NOT ACTIVE | NOT ACTIVE | NOT ACTIVE |
| NV1055 | NOT ACTIVE | NOT ACTIVE | NOT ACTIVE | NOT ACTIVE | NOT ACTIVE | NOT ACTIVE |
| NV1056 | NOT ACTIVE | NOT ACTIVE | NOT ACTIVE | NOT ACTIVE | NOT ACTIVE | NOT ACTIVE |
| NV1057# | NOT ACTIVE | NOT ACTIVE | NOT TESTED | NOT TESTED | NOT TESTED | NOT TESTED |
| NV1058 | NOT ACTIVE | NOT ACTIVE | NOT ACTIVE | NOT ACTIVE | NOT ACTIVE | NOT ACTIVE |
| NV1059 | NOT ACTIVE | NOT ACTIVE | NOT ACTIVE | NOT ACTIVE | NOT ACTIVE | NOT ACTIVE |
| NV1060 | NOT ACTIVE | NOT ACTIVE | NOT ACTIVE | NOT ACTIVE | NOT ACTIVE | NOT ACTIVE |
| NV1061 | 0.878 | 5.629 | 2.143 | >10 | 1.152 | 9.518 |
| NV1062 | 0.199 | 0.400 | NOT ACTIVE | NOT ACTIVE | 0.273 | 0.608 |
| NV1063 | 0.137 | 0.334 | NOT ACTIVE | NOT ACTIVE | 0.100 | 0.189 |
| NV1064 | 1.295 | 4.062 | NOT ACTIVE | NOT ACTIVE | 0.688 | 1.338 |

TABLE 5-continued

Activity of polyamides against HPV

| NanoVir # | HPV16 IC50 [μM] | HPV16 IC90 [μM] | HPV18 IC50 [μM] | HPV18 IC90 [μM] | HPV31 IC50 [μM] | HPV31 IC90 [μM] |
|---|---|---|---|---|---|---|
| NV1065 | NOT ACTIVE | NOT ACTIVE | NOT ACTIVE | NOT ACTIVE | NOT ACTIVE | NOT ACTIVE |
| NV1066 | 0.132 | 0.835 | 0.280 | 1.589 | 0.141 | 1.747 |
| NV1067 | 0.409 | 1.210 | 0.389 | 2.092 | 0.205 | 2.119 |
| NV1068 | 0.220 | 2.311 | 0.516 | 5.205 | 0.314 | 4.067 |
| NV1069 | 0.725 | 2.257 | 1.509 | 8.744 | 0.363 | 0.894 |
| NV1070 | 0.308 | 4.898 | 0.459 | 10 | 0.398 | 2.157 |
| NV1071 | 0.255 | 2.317 | 0.093 | 3.809 | 0.095 | 1.597 |
| NV1072 | 0.109 | >10 | 0.216 | >10 | 0.096 | 10 |
| NV1073 | 0.267 | 10 | 0.405 | >10 | 0.220 | >10 |
| NV1074 | 0.178 | 1.749 | 0.041 | 0.192 | 0.052 | 0.320 |
| NV1075 | 0.124 | 2.627 | 0.049 | 0.314 | 0.056 | 0.546 |
| NV1076 | 0.067 | 0.594 | 0.048 | 0.236 | 0.104 | 0.403 |
| NV1077 | 0.095 | 0.410 | 0.015 | 0.094 | 0.032 | 0.181 |
| NV1078 | 0.046 | 0.307 | 0.030 | 0.091 | 0.047 | 0.176 |
| NV1079 | 0.041 | 0.152 | 0.023 | 0.115 | 0.041 | 0.150 |
| NV1080 | 0.058 | 0.288 | 0.037 | 0.113 | 0.073 | 0.168 |
| NV1081 | NA | NA | NA | NA | NA | NA |
| NV1082 | NA | NA | NA | NA | NA | NA |
| NV1083 | 2.41 | >10 | 0.929 | >10 | 3.082 | >10 |
| NV1084 | 1.91 | >10 | 1.041 | >10 | 7.325 | >10 |
| NV1085 | 0.029 | 0.353 | 0.041 | 0.201 | 0.032 | 0.213 |
| NV1086 | 0.043 | 0.212 | 0.062 | 0.174 | 0.016 | 0.174 |
| NV1087 | 0.031 | 0.200 | 0.024 | 0.297 | 0.016 | 0.135 |
| NV1088 | 0.02 | 0.180 | 0.035 | 0.157 | 0.014 | 0.136 |
| NV1089 | 0.068 | 0.265 | 0.068 | 0.169 | 0.046 | 0.217 |
| NV1090 | 0.051 | 0.215 | 0.053 | 0.617 | 0.022 | 0.157 |
| NV1092 | 0.169 | 0.962 | 2.9 | >10 | 0.03 | 0.088 |
| NV1093 | 0.072 | 0.970 | 0.085 | 2.6 | 0.042 | 0.335 |
| NV1094 | NOT ACTIVE | NOT ACTIVE | NOT ACTIVE | NOT ACTIVE | NOT ACTIVE | NOT ACTIVE |
| NV1095 | 0.204 | 2.196 | NOT ACTIVE | NOT ACTIVE | 0.049 | 0.324 |
| NV1096 | 0.024 | 0.138 | 0.036 | 0.348 | 0.035 | 0.090 |
| NV1097 | 0.07 | 1.407 | 0.257 | >10 | 0.04 | 10 |
| NV1098 | 0.011 | 1.360 | 0.017 | >10 | 0.024 | 0.549 |
| NV1101 | NOT TESTED | NOT TESTED | NOT TESTED | NOT TESTED | NOT TESTED | NOT TESTED |
| NV1102 | NOT ACTIVE | NOT ACTIVE | NOT ACTIVE | NOT ACTIVE | NOT ACTIVE | NOT ACTIVE |
| NV1103 | NOT ACTIVE | NOT ACTIVE | NOT ACTIVE | NOT ACTIVE | NOT ACTIVE | NOT ACTIVE |
| NV1104 | NOT ACTIVE | NOT ACTIVE | NOT ACTIVE | NOT ACTIVE | NOT ACTIVE | NOT ACTIVE |
| NV1105 | NOT ACTIVE | NOT ACTIVE | NOT ACTIVE | NOT ACTIVE | NOT ACTIVE | NOT ACTIVE |
| NV1106 | 6.7 | NOT TESTED | NOT ACTIVE | NOT ACTIVE | 1.4 | NOT TESTED |
| NV1107 | 0.028 | 0.180 | 0.025 | 0.340 | 0.018 | 0.276 |
| NV1108 | 0.212 | 0.718 | 0.513 | >10 | 0.673 | 6.752 |
| NV1109 | 0.055 | 0.293 | 0.075 | 0.290 | 0.045 | 0.267 |
| NV1110 | 0.43 | 4.445 | 0.921 | >10 | 0.825 | >10 |
| NV1111 | 0.017 | 0.121 | 0.018 | 0.136 | 0.004 | 0.079 |
| NV1112 | 0.047 | 0.195 | 0.057 | 0.324 | 0.022 | 0.151 |
| NV1113 | 0.304 | >10 | 0.228 | >10 | 0.125 | 0.888 |
| NV1114 | 0.035 | 0.411 | 0.036 | 0.125 | 0.009 | 0.085 |
| NV1115 | 0.103 | 0.378 | 0.167 | 0.937 | 0.139 | 0.752 |
| NV1116 | 0.038 | 0.340 | 0.029 | 0.142 | 0.016 | 0.127 |
| NV1117 | NOT ACTIVE | NOT ACTIVE | NOT ACTIVE | NOT ACTIVE | NOT ACTIVE | NOT ACTIVE |
| NV1118 | 0.018 | 0.245 | 0.007 | 0.254 | 0.017 | 0.162 |
| NV1119 | 0.058 ± 0.009 | 0.553 ± 0.154 | 0.027 ± 0.0001 | 0.191 ± 0.002 | 0.035 ± 0.00002 | 0.106 ± 0.0005 |
| CHC2001 | 0.026 ± 0.004 | 0.299 ± 0.082 | 0.106 ± 0.002 | 1.489 ± 1.234 | 0.072 ± 0.003 | 0.384 ± 0.019 |
| CHC2002 | 0.636 ± 0.606 | 2.305 ± 7.486 | 0.758 | >10 | 0.058 ± 0.009 | 0.341 ± 0.470 |
| KJK6045f26-28 | 0.817 ± 0.535 | 2.279 ± 6.981 | 8.726 | >10 | 1.775 ± 9.062 | >10 |
| KJK6047-1 | 1.471 ± 15.186 | >10 | 6.011 ± 4.571 | >10 | 1.046 ± 6.472 | >10 |
| KJK6048 | 2.048 | >10 | 9.172 | >10 | 1.859 ± 6.809 | 7.344 ± 15.156 |
| KJK6049 | 0.435 ± 0.073 | 2.249 ± 7.107 | >10 | >10 | 0.258 ± 0.040 | 1.253 ± 0.189 |

TABLE 5-continued

Activity of polyamides against HPV

| NanoVir # | HPV16 IC50 [μM] | HPV16 IC90 [μM] | HPV18 IC50 [μM] | HPV18 IC90 [μM] | HPV31 IC50 [μM] | HPV31 IC90 [μM] |
|---|---|---|---|---|---|---|
| KJK6050f16-18 | 0.400 ± 0.426 | 3.035 ± 12.939 | 0.259 ± 0.113 | 5.916 | 0.664 ± 2.507 | 1.688 ± 18.426 |
| KJK6062 | 0.227 ± 0.036 | 2.966 ± 9.136 | 0.155 ± 0.001 | >10 | 0.518 ± 0.352 | 1.876 ± 5.317 |
| KJK6065f17-19 | 0.066 ± 0.009 | 0.472 ± 0.136 | 2.456 ± 4.818 | >10 | 0.571 ± 0.111 | 2.233 ± 3.395 |
| KJK6067f12 | 0.191 ± 0.006 | 2.331 ± 2.506 | 0.979 ± 1.496 | 4.007 ± 5.165 | 0.445 ± 0.171 | 1.518 ± 11.392 |
| KJK6068f20-22 | 1.556 | >10 | 1.151 ± 1.887 | >10 | 0.407 ± 0.0002 | 1.151 ± 0.011 |
| KJK6076 | 0.047 ± 0.001 | 0.187 ± 0.005 | 0.041 ± 0.0003 | 0.147 ± 0.019 | 0.019 ± 0.0001 | 0.090 ± 0.0003 |
| KJK6099 | 0.289 ± 0.058 | >10 | 6.462 | >10 | 0.403 ± 0.031 | 2.145 ± 0.193 |
| NV1042 FT1138 FT1139 | 0.036 | 0.351 | 0.056 | 1.462 | 0.030 | 0.510 |

In Table 5, "NA" or "NOT ACTIVE" indicates no measurable antiviral response was obtained relative to control at the highest dose tested (10 μM).
The $IC_{50}$ is the concentration of compound required for 50% decrease of viral DNA concentration in vitro.
The $IC_{90}$ is the concentration of compound required for 90% decrease in viral DNA concentration in vitro.

The results demonstrate that the polyamides of the invention exhibited effectiveness in inhibiting replication of HPV16, HPV18 and HPV31. Thus, the polyamides of the invention are demonstrated to exhibit activity against HPV in human cells which are infected with HPV and may represent an effective therapeutic agent for the treatment of patients infected with HPV or other papillomaviruses.

Polyamides designated in Table 5 as KJK6045f26-28; KJK6047-1; KJK6050f16-18; KJK6062; KJK6065f17-19; and KJK6067f12 are TMG or unsubstituted guanidine (Guan) derivatives.

The data show that the compounds with high anti-HPV $IC_{90}$ values are TMG and unsubstituted guanidine (Guan) derivatives. An $IC_{90}$ value is the single most important metric used in the antiviral drug discovery arena, and the fact that TMG and unsubstituted guanidine (Guan) derivatives exhibit high $IC_{90}$ values is surprising and is in no way predictable from the prior art.

What is more, the results show that N-terminal substitution of an anti-HPV polyamide with unsubstituted Guan or substituted Guan derivatives improves the antiviral activities against the two most prevalent high-risk HPV types (HPV16 and -18). Upon N-terminal substitution with a tetramethylguanidinium group, improvement in anti-HPV activity ($IC_{50}$) was observed against HPV18.

Polyamides designated in Table 5 as CHC2001; CHC2002; KJK6045f26-28; KJK6047-1; KJK6048; KJK6049; KJK6050f16-18; KJK6062; KJK6065f17-19; KJK6067f12; KJK6068f20-22; KJK6076; FT1138; and FT1139, are formate salts of polyamide compounds.

Moreover, the compounds of the invention include formate salts of polyamide compounds. Table 5 shows the anti-viral activity of the polyamide compound NV1028 as well as the formate salts of NV1028 which is designated as CHC2001. Moreover, Table 5 shows the anti-viral activity of NV1042 as well at the formate salts of NV1042 designated as KJK6076.

Surprisingly, the polyamide compounds in the form of a formate salt exhibit enhanced activity over those compounds which are not in the formate salt form. For example, a comparison of the 1090 value of NV1028 and CHC2001 demonstrates a nearly 4-fold increase in the 1090 value when the polyamide is in the formate salt form. Such enhanced antiviral activity observed with the formate salt form of the polyamide is unexpected and may not be predicted based on the use of formate salts in chemical synthesis per se.

What is more, is was observed that NV1106 exhibits anti-viral activity, which anti-viral activity is remarkable given that NV1106 is only an 8-ring polyamide.

Several alternative approaches may be used to confirm the effects of the compounds on viral DNA. These additional procedures include normalization to total DNA, preparation of DNA by different procedures including DNeasy (Total Genomic DNA) Qiagen spin columns, DNAzol total genomic DNA preparations, and Hirt (low MW DNA preparations; (Hirt, (1967), J Mol Biol. 26:365-9).

Southern blotting may be used to confirm the effects of polyamides on HPV DNA levels that were determined using real-time PCR technology. The experiments may be conducted as previously described (Gamer-Hamrick and Fisher, Virology, 301, 334-41, 2002).

The toxicity of each polyamide found active against HPV may be monitored in normal human keratinocytes using an MTT cell viability assay (Denizot and Lang, 1986).

In order that the invention described herein may be more fully understood, the following examples are set forth. It should be understood that these examples are for illustrative purposes only and are not to be construed as limiting this invention in any manner.

EXAMPLES

Example 1: A Single Polyamide Dose Impedes Infection by Polyomavirus and Promotes Cell Survival A representative polyamide, NV1042, was prepared. BS-C-1 cells were plated at $5 \times 10^5$ cells per well in 24-well plates in culture media composed of 10% FBS plus 50 U/mL penicillin-streptomycin (Life Technologies, cat #15070063). Upon reaching 90-100% confluency, SV40 virus was diluted in MEM-2% FBS and 50 μL was applied per well at a multiplicity of infection (MOI) equal to 1. Virus was allowed to adhere to cells for 2 h at 37° C. in a humidified incubator with 5% $CO_2$ at which time virus was removed and 0.5 mL MEM-2% FBS was added to each well. Infection was allowed to proceed for 24 h before 10 µM NV1042 in 0.1% DMSO was added to culture wells and incubated an additional 72 h before being removed by a change of media. The effects of polyamide treatment was followed for up to 12 days post-infection. The cells were examined each day for effects on cell survival and substratum adherence (a measure of viability). Cells that were not infected by SV40 showed no signs of cell death or loss, while SV40 infected cells began dying due to viral cytopathic effect (CPE) by 6-7 days post infection. By 9 days post-infection the virus-induced death of cells was complete and no adherent cells remained. On the other hand, the single polyamide treatment resulted in significant protection of cells from CPE so that even by 12 days post-infection cell survival was clearly noticeable.

A study of SV40 virus DNA levels over the 12 day period of infection clearly demonstrated that the single polyamide treatment potently blocked viral DNA propagation. Following the initial infection, DNA was extracted each day from all adherent and floating cells with DNAzol (Life Technologies, cat #10503-027) according to the manufacturer's recommendation. Q-PCR reaction mixtures contained 8 µL sample DNA, 200 nM each primer, 250 nM probe and 10 µL 2× Master Mix (LightCycler 480 Probes Master; Roche, cat #04887301001) in a total volume of 20 pt. Samples were analyzed using instrumentation purchased from Roche (LightCycler 480). Drug effects on viral DNA copy number were calculated as a percentage of viral DNA copies quantified in the DMSO-treated cells (standard-curve method), the log-dose response plotted, and $IC_{50}$s calculated using best-curve fitting software (XLfit; IDBS, United Kingdom). The primers and probe for SV40 were as follows: forward 5'-CCTCCGTTAAGGTTCGTAGGTCA-3' (SEQ ID NO:1), reverse 5'-CAGCGCTCACACCAGTC-3' (SEQ ID NO:2) probe 5'-/56-FAM-ATTGAAGTGCAACTTG-CATCTGTTGCTACTGTTGA-3BHQ_1/-3' (SEQ ID NO:3). Cycling conditions: 10 min at 95° C. followed by 40 cycles of 95° C. for 30 sec and 60° C. for 60 sec. A single polyamide treatment caused a profound inhibition of viral DNA levels for the period of infection relative to the untreated cells so that by day 12 (11 days after polyamide treatment) only 25% of the viral DNA levels found in the untreated samples was present in the treated samples.

The delay in virus propagation was clearly evident and demonstrable by following the expression of large T antigen (LT, the primary transforming protein of SV40 involved in virus replication) and phosphorylation of ATM, the DNA repair protein activated by SV40 and large T antigen. Cells were fixed in 3.7% paraformaldehyde for 5 min at RT and washed three times with PBS. Cells were then permeabilized in 0.2% Triton X-100 in PBS for 5 min at RT and washed 3× with PBS. Prior to IF, nonspecific antigen binding was blocked by incubation of cells with 3% BSA in PBS for 30 min at RT. Primary antibody dilutions were prepared in 1% BSA-PBS; LT-ag was localized with PAb416 (Abcam, cat #ab16879) at 1:200 dilution and Phospho S1981 ATM (pATM) with EP1890Y (Abcam, cat #ab81292) at 1:250 dilution with RT incubation for 2 h. Coverslips were washed 3× for 10 min each with PBS. Secondary antibodies were diluted in 1% BSA-PBS at 1:500 dilution; LgT-ag was detected with goat anti-mouse AlexaFluor 546 (Life Technologies, cat #A11056) and pATM with goat anti-rabbit AlexaFluor 488 (Life Technologies, cat #A11055). Coverslips were incubated with secondary antibodies for 2 h at RT and then washed 3×10 min each with PBS. Total nuclei were visualized by staining with DAPI contained in the mounting solution (ProLong Gold with DAPI; Life Technologies, cat #P36931). Expression of LT and pATM were both significantly delayed following the single polyamide treatment in a manner that reflected both the delay in cell death and viral DNA propagation. The results were quantifiable and correlated well with cell loss from CPE and cell protection by the polyamide.

Example 2: Effects of Representative Polyamides on Various DNA Viruses

The effects of polyamides were tested on a variety of DNA viruses that were either maintained in cells as episomes (HPV16 in W12 cells or EBV in Raji cells) or were introduced into cells following infection (BKV and SV40). For SV40: BS-C-1 cells were plated at $5\times10^5$ cells per well in 24-well plates. Upon reaching 90-100% confluency, SV40 virus was diluted in MEM-2% FBS and 50 µL was applied per well at a MOI equal to 1. Virus was allowed to adhere to cells for 2 h at 37° C. in a humidified incubator with 5% $CO_2$ at which time virus was removed and 0.5 mL MEM-2% FBS was added to each well. Infection was allowed to proceed for 24 h before increasing doses of PA from 0.001-10 µM or 0.1% DMSO was added to culture wells and incubated an additional 48 h. Following the treatment period, DNA was extracted with DNAzol (Life Technologies, cat #10503-027) according to the manufacturer's recommendation. For BKV: RPTEC cells were plated at $1\times10^5$ cells per well in 24-well plates in renal epithelial cell growth medium (REGM; ATCC-PCS-400-030) supplemented with recombinant human epidermal growth factor (10 ng/mL), triiodothyronine (10 nM), hydrocortisone (100 ng/mL), recombinant human insulin (5 µg/mL), epinephrine (1 µM), transferrin (5 µg/mL), 0.5% fetal bovine serum (renal epithelial cell growth kit; ATCC-PCS-400-040) and GA-1000 (30 µg/mL gentamicin and 15 ng/mL amphotericin B; Lonza cat #CC4083). When confluent, cells were infected with 50 µl BKV-TU or BKV-DUN per well at an MOI of 0.5 FFU/mL diluted in REGM with 0.5% FBS. Following 2 h incubation, virus inoculum was removed and replaced with 500 µL of fresh REGM-0.5% FBS. BKV infected RPTEC cells were cultured for 48 h and then increasing doses of PA from 0.001-10 µM or 0.1% DMSO was added to culture wells and incubated an additional 48 h, at which time DNA was extracted with DNAzol. For EBV: Raji cells were cultured in 12-well plates at a density of $2\times10^5$ cells/mL in RPMI-10% FBS containing either increasing doses of PA from 0.001-10 µM or a vehicle control of 0.1% DMSO. Following a 48 h treatment period, cells were centrifuged at 1000 rpm for 3 min and DNA extracted with DNAzol. DNA concentration and purity was determined spectrophotometrically and diluted to 20 ng in 8 µL $dH_2O$ for Q-PCR.

HPV16 DNA episomes were studied in W12 cells as previous described (33).

The smaller viruses (HPV, SV40, and BKV) all responded to the test polyamide NV1042 with $IC_{50}$'s in the low nanomolar range, indicating that these viruses are good therapeutic targets for polyamide NV1042 and related polyamides and polyamide classes described herein.

Moreover, the low nanomolar $IC_{50}$ range indicates that the compounds may be administered in a therapeutically effective amount for efficacious treatment of human papillomavirus and polyomavirus infected subjects/patients.

Example 3: $IC_{50}$'s and $IC_{90}$'s of Polyamides Tested Against SV40 and BKV A series of polyamides was tested in antiviral assays against polyomaviruses as described above. Table 4 ranks the polyamides by potency ($IC_{50}$) against the prototypical polyomavirus SV40. The two polyamides not tested against SV40, NV1089 and NV1090, were highly potent against representative BKV strains. In general, if a polyamide demonstrated good activity against SV40 it also exhibited potent activity against BKV. Conversely, those polyamides with poor activity against SV40 (>0.5 $\mu IC_{50}$) also showed poor or no activity against BKV. For polyamides tested and listed in Table 4 and Table 5, the sequences are shown in Table 1 and their high resolution mass spectral data are given in Table 2 and Table 3 for verifying composition.

From these results, one skilled in the art may conclude that the polyamides of the invention would provide therapeutic efficacy in clinically relevant polyomaviruses.

Example 4

Polyamides may work through a mechanism that involves the DNA damage response (DDR) and inhibition of members of DDR pathways that regulate DNA strand break repair act as polyamide enhancers.

BS-C-1 and RPTEC cells were plated and infected as above with SV40 and BKV respectively. After 24 h increasing doses of NV1042 from 0.001-10 μM was added in the presence or absence of 100 μM Mirin (Sigma, cat #M9948; an inhibitor of MRE11) or 0.1% DMSO was added for an additional 48 h. At the end of the treatment period, total DNA was harvested with DNAzol and 20 ng total DNA analyzed by Q-PCR. These studies demonstrate that the $IC_{50}$ of polyamide against 2 different polyomaviruses, SV40 and BKV, is enhanced (i.e. lowered) by inhibition of Mre11, which is important for ssDNA and dsDNA break repair (34).

Inhibitors of Chk2 also acted as enhancers of polyamide activity. BS-C-1 cells were seeded at $4 \times 10^5$ cells per 60 mm dish and cultured for 72 h until 90-100% confluent. Cells were infected with SV40 virus in MEM+2% FBS for 2 h at 37° C. (200 μL virus/p60 at 100 pfu/mL; MOI=0.00001), at which time virus-containing media was removed and cells incubated with fresh media for 24 h. Virus-infected cells were then treated with 0.1% DMSO, 1 μM NV1042, 10 μM NV1042, 5 μM Chk2-inhibitor (Chk2-I; Sigma, cat #C3742). Media was changed after 4 days of drug treatment and cultures maintained for an additional 10 days. Plates were then stained for 10' with 0.1% Crystal Violet (Ted Pella, cat #18711) plus 1% formaldehyde, 1% Methanol, and PBS, rinsed with tap water until water ran clear and air-dried and photographed. Chk2-I acted to enhance the antiviral activity of 1 μM NV1042 as evidenced by the protection of BS-C-1 cells from SV40 CPE relative to 1 μM NV1042 alone.

Example 5: Effects of Representative Polyamides on HPV

A series of polyamides are tested in antiviral assays against human papillomavirus. The antiviral activities are calculated by measuring the ability of the polyamide compounds to decrease the HPV viral episomal load in monolayer keratinocyte cultures. The episomal load is determined by Q-PCR.

The potency ($IC_{50}$ and $IC_{90}$) of the polyamides of the invention against HPV is evaluated as described above. As shown in Table 5, the polyamides of the invention exhibit activity against HPV in human cells which are infected with HPV. Thus, the polyamides of the invention may represent an effective therapeutic agent for the treatment of patients infected with HPV.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

REFERENCES

1. Eddy B E, Borman G S, Berkeley W H, Young R D. Tumors induced in hamsters by injection of rhesus monkey kidney cell extracts. Proceedings of the Society for Experimental Biology and Medicine Society for Experimental Biology and Medicine. 1961; 107:191-7. Epub 1961/05/01. PubMed PMID: 13725644.
2. DeCaprio J A, Garcea R L. A cornucopia of human polyomaviruses. Nat Rev Microbiol. 2013; 11(4):264-76. Epub 2013/03/12. doi: 10.1038/nrmicro2992. PubMed PMID: 23474680.
3. Dalianis T, Hirsch H H. Human polyomaviruses in disease and cancer. Virology. 2013; 437(2):63-72. Epub 2013/01/30. doi: 10.1016/j.virol.2012.12.015. PubMed PMID: 23357733.
4. Hirsch H H, Randhawa P. B K polyomavirus in solid organ transplantation. American journal of transplantation: official journal of the American Society of Transplantation and the American Society of Transplant Surgeons. 2013; 13 Suppl 4:179-88. Epub 2013/03/08. doi: 10.1111/ajt.12110. PubMed PMID: 23465010.
5. Bennett S M, Broekema N M, Imperiale M J. B K polyomavirus: emerging pathogen. Microbes and infection/Institut Pasteur. 2012; 14(9):672-83. Epub 2012/03/10. doi: 10.1016/j.micinf.2012.02.002. PubMed PMID: 22402031; PubMed Central PMCID: PMC3568954.
6. Dropulic L K, Jones R J. Polyomavirus B K infection in blood and marrow transplant recipients. Bone Marrow Transplant. 2008; 41(1):11-8. Epub 2007/10/24. doi: 10.1038/sj.bmt.1705886. PubMed PMID: 17952131; PubMed Central PMCID: PMC3066131.
7. De Gascun C F, Carr M J. Human polyomavirus reactivation: disease pathogenesis and treatment approaches. Clin Dev Immunol. 2013; 2013:373579. Epub 2013/06/06. doi: 10.1155/2013/373579. PubMed PMID: 23737811; PubMed Central PMCID: PMC3659475.
8. Ezzikouri S, Ozawa M, Kohara M, Elmdaghri N, Benjelloun S, Tsukiyama-Kohara K. Recent insights into hepatitis B virus-host interactions. J Med Virol. 2014; 86(6):925-32. Epub 2014/03/08. doi: 10.1002/jmv.23916. PubMed PMID: 24604126.
9. McMahon B J. Epidemiology and natural history of hepatitis B. Semin Liver Dis. 2005; 25 Suppl 1:3-8. Epub 2005/08/17. doi: 10.1055/s-2005-915644. PubMed PMID: 16103976.
10. WHO. Hepatitis B Fact Sheet. http://wwwwhoint/mediacentre/factsheets/fs204/en/. 2013.
11. De Clercq E, Ferir G, Kaptein S, Neyts J. Antiviral treatment of chronic hepatitis B virus (HBV) infections. Viruses. 2010; 2(6):1279-305. Epub 2010/06/01. doi: 10.3390/v2061279. PubMed PMID: 21994680; PubMed Central PMCID: PMC3185710.

12. Chisari F V, Mason W S, Seeger C. Virology. Comment on "Specific and nonhepatotoxic degradation of nuclear hepatitis B virus cccDNA". Science. 2014; 344(6189): 1237. Epub 2014/06/14. doi: 10.1126/science.1254082. PubMed PMID: 24926010.
13. Lucifora J, Xia Y, Reisinger F, Zhang K, Stadler D, Cheng X, et al. Specific and nonhepatotoxic degradation of nuclear hepatitis B virus cccDNA. Science. 2014; 343(6176):1221-8. Epub 2014/02/22. doi: 10.1126/science.1243462. PubMed PMID: 24557838.
14. Xia Y, Lucifora J, Reisinger F, Heikenwalder M, Protzer U. Virology. Response to Comment on "Specific and nonhepatotoxic degradation of nuclear hepatitis B virus cccDNA". Science. 2014; 344(6189):1237. Epub 2014/06/14. doi: 10.1126/science.1254083. PubMed PMID: 24926011.
15. Baird E E, Dervan P B, inventors; (California Institute of Technology, USA). assignee. Stereochemical control of the DNA binding affinity, sequence specificity, and orientation-preference of chiral hairpin polyamides in the minor groove. Wo patent 9845284. 1998.
16. Wang C C C, Ellervik U, Dervan P B. Expanding the recognition of the minor groove of DNA by incorporation of β-alanine in hairpin polyamides. Bioorg Med Chem. 2001; 9(3):653-7.
17. White S, Baird E E, Dervan P B. On the pairing rules for recognition in the minor groove of DNA by pyrrole-imidazole polyamides. Chem Biol. 1997; 4(8):569-78.
18. White S, Baird E E, Dervan P B. Effects of the A.T/T.A degeneracy of pyrrole—imidazole polyamide recognition in the minor groove of DNA. Biochemistry. 1996; 35(38): 12532-7.
19. Pilch D S, Poklar N, Gelfand C A, Law S M, Breslauer K J, Baird E E, et al. Binding of a hairpin polyamide in the minor groove of DNA: sequence-specific enthalpic discrimination. Proc Natl Acad Sci USA. 1996; 93(16): 8306-11.
20. Pilch D S, Poklar N, Baird E E, Dervan P B, Breslauer K J. The thermodynamics of polyamide-DNA recognition: hairpin polyamide binding in the minor groove of duplex DNA. Biochemistry. 1999; 38(7):2143-51.
21. Kielkopf C L, White S, Szewczyk J W, Turner J M, Baird E E, Dervan P B, et al. A structural basis for recognition of A. T and T. A base pairs in the minor groove of B-DNA. Science. 1998; 282(5386):111-5. PubMed PMID: 1998429643.
22. Melander C, Herman D M, Dervan P B. Discrimination of A/T sequences in the minor groove of DNA within a cyclic polyamide motif. Chem—Eur J. 2000; 6(24):4487-97.
23. Urbach A R, Love J J, Ross S A, Dervan P B. Structure of a Beta-alanine-linked Polyamide Bound to a Full Helical Turn of Purine Tract DNA in the 1:1 Motif. J Mol Biol. 2002; 320(1):55-71. PubMed PMID: An 2002: 472418.
24. Parks M E, Baird E E, Dervan P B. Optimization of the Hairpin Polyamide Design for Recognition of the Minor Groove of DNA. J Am Chem Soc. 1996; 118(26):6147-52. PubMed PMID: AN 1996:354121.
25. Trauger J W, Baird E E, Mrksich M, Dervan P B. Extension of Sequence-Specific Recognition in the Minor Groove of DNA by Pyrrole-Imidazole Polyamides to 9-13 Base Pairs. J Am Chem Soc. 1996; 118(26):6160-6. PubMed PMID: AN 1996:354122.
26. Urbach A R, Dervan P B. Toward rules for 1:1 polyamide:DNA recognition. Proc Natl Acad Sci USA. 2001; 98(8):4343-8.
27. Schaal T D, Mallet W G, McMinn D L, Nguyen N V, Sopko M M, John S, et al. Inhibition of human papillomavirus E2 DNA binding protein by covalently linked polyamides. Nucleic Acids Res. 2003; 31:1282-91.
28. Nguyen-Hackley D H, Ramm E, Taylor C M, Joung J K, Dervan P B, Pabo C O. Allosteric Inhibition of Zinc-Finger Binding in the Major Groove of DNA by Minor-Groove Binding Ligands. Biochemistry. 2004; 43(13): 3880-90. PubMed PMID: AN 2004:202580.
29. Fechter E J, Dervan P B. Allosteric inhibition of protein-DNA complexes by polyamide-intercalator conjugates. J Am Chem Soc. 2003; 125(28):8476-85. PubMed PMID: An 2003:466838.
30. Dickinson L A, Trauger J W, Baird E E, Dervan P B, Graves B J, Gottesfeld J M. Inhibition of Ets-1 DNA binding and ternary complex formation between Ets-1, NF-kappaB, and DNA by a designed DNA-binding ligand. J Biol Chem. 1999; 274(18):12765-73.
31. Weisz K. Polyamides as artificial regulators of gene expression. Angew Chem, Int Ed Engl. 1997; 36(23): 2592-4.
32. Supekova L, Pezacki J P, Su A I, Loweth C J, Riedl R, Geierstanger B, et al. Genomic Effects of Polyamide/DNA Interactions on mRNA Expression. Chem Biol. 2002; 9(7):821-7. PubMed PMID: An 2002:561865.
33. Edwards T G, Koeller K J, Slomczynska U, Fok K, Helmus M, Bashkin J K, et al. HPV episome levels are potently decreased by pyrrole-imidazole polyamides. Antiviral research. 2011; 91(2):177-86. Epub 2011/06/15. doi: 10.1016/j.antiviral.2011.05.014. PubMed PMID: 21669229.
34. Dupre A, Boyer-Chatenet L, Sattler R M, Modi A P, Lee J H, Nicolette M L, et al. A forward chemical genetic screen reveals an inhibitor of the Mre11-Rad50-Nbs1 complex. Nature chemical biology. 2008; 4(2):119-25. Epub 2008/01/08. doi: 10.1038/nchembio.63. PubMed PMID: 18176557; PubMed Central PMCID: PMC3065498.

The invention claimed is:

1. A compound of the formula:
Guan-PPPβPPβPIm-γ-PβPPβPPPβPβTa;
Guan-PPPβPPβPIm-γ-PβPPβPPPβPβDp;
Guan-PPβPPImβPP-γ-PPβPPPβPPPβTa;
Guan-IPPβPPIβPP-γ-PPβPPPβPPPβTa;
Guan-PPβPPImβPP-γ-PPβPPPβPPPβDp;
Guan-IPPβPPP-γ-PPβPPPPβTa;
Guan-PPβPPP-γ-PPβPPPPβTa;
or
Guan-PPβPPP-γ-PPβPPPPβDp,
wherein GUAN=a guanidinyl radical of the formula:

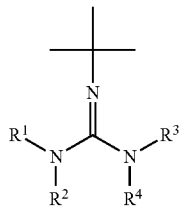

or its tautomer, wherein $R^1$, $R^2$, $R^3$, or $R^4$ is H, alkyl, aryl or aralkyl;

P=4-amino-2-carbonyl-N-methylpyrrole; γ=gamma-aminobutyric acid;

β=beta-alanine; I or Im=4-amino-2-carbonyl-N-methylimidazole;

Ta=3,3'-diamino-N-methyldipropylamine; and Dp=(dimethylamino)propylamine.

2. The compound of claim 1 which is in the form of a formate salt.

3. A pharmaceutical composition comprising a compound of claim 1 in a therapeutically amount effective for the treatment of polyomavirus infected cells, and a pharmaceutically acceptable carrier.

4. A method of treating cells infected with a polyomavirus comprising administering to a subject infected with the polyomavirus, a therapeutically effective amount of a compound of claim 1.

* * * * *